(12) United States Patent
Bark et al.

(10) Patent No.: US 9,439,910 B2
(45) Date of Patent: Sep. 13, 2016

(54) FE(III)-PYRAZINE COMPLEX COMPOUNDS FOR TREATMENT AND PROPHYLAXIS OF IRON-DEFICIENCY PHENOMENA AND IRON-DEFICIENCY ANAEMIA

(71) Applicant: VIFOR (INTERNATIONAL) AG, St. Gallen (CH)

(72) Inventors: Thomas Bark, Zurich (CH); Wilm Buhr, Constance (DE); Susanna Burckhardt, Zurich (CH); Michael Burgert, Friedrichshafen (DE); Camillo Canclini, St. Gallen (CH); Franz Dürrenberger, Dornach (CH); Felix Funk, Winterthur (CH); Peter Otto Geisser, St. Gallen (CH); Aris Kalogerakis, Winterthur (CH); Simona Mayer, Bühler (CH); Erik Philipp, Arbon (CH); Stefan Reim, Stadel Winterthur (CH); Diana Sieber, Abtwil (CH); Jörg Schmitt, Thal (CH); Katrin Schwarz, St. Gallen (CH)

(73) Assignee: VIFOR (INTERNATIONAL) AG, St. Gallen (CH)

( * ) Notice: Subject to any disclaimer, the term of this patent is extended or adjusted under 35 U.S.C. 154(b) by 0 days.

(21) Appl. No.: 14/390,781

(22) PCT Filed: Apr. 4, 2013

(86) PCT No.: PCT/EP2013/057071
§ 371 (c)(1),
(2) Date: Oct. 4, 2014

(87) PCT Pub. No.: WO2013/150087
PCT Pub. Date: Oct. 10, 2013

(65) Prior Publication Data
US 2015/0119374 A1    Apr. 30, 2015

(30) Foreign Application Priority Data
Apr. 5, 2012    (EP) .................................... 12163308

(51) Int. Cl.
*A61K 31/555* (2006.01)
*C07D 241/18* (2006.01)
*C07F 15/02* (2006.01)

(52) U.S. Cl.
CPC ........... *A61K 31/555* (2013.01); *C07D 241/18* (2013.01); *C07F 15/025* (2013.01)

(58) Field of Classification Search
CPC ..................................................... A61K 31/555
USPC .................................................. 514/184, 186
See application file for complete search history.

(56) References Cited

FOREIGN PATENT DOCUMENTS

EP          0120670 A1    10/1984

OTHER PUBLICATIONS

Zhu et al. Natural Products Communications (2011), 6(8), 1137-1140.*
Ohkanda et al. Bulletin of the Chemical Society of Japan (1993), 66(3), 841-7.*
Maebayashi et al. Chemical & Pharmaceutical Bulletin (1978), 26(4), 1320-2.*
Feng Zhu et al, Natural Product Communications, 6(8), 1137-1140, 2011.
Ohkanda et al, Tetrahedron, Elsevier Science Publishers, 51(47), pp. 12995-13002, 1995.
Junko Ohkanda et al, J. Org. Chem, pp. 3618-3624, 1997.
J Ohkanda et al, Bulletin of the Chemical Society of Japan, vol. 66, pp. 841-847, 1993.
Yukio Maebayashi et al, Chemical & Pharmaceutical Bulletin, pp. 1320-1322, 1978.
Jing Hao et al, Chemical & Pharmaceutical Bulletin, pp. 277-279, 1994.
Arai Kunizo et al, Chemical & Pharmaceutical Bulletin, pp. 1510-1517, 1981.
Gemma Assante et al, Journal of Agricultural and Food Chemistry, pp. 785-787, 1981.
Jing Hao et al, Heterocycles, Elsevier Science Publishers, 35(2), pp. 1279-1287, 1993.
Sachiko Suzuki et al, International Journal for Vitamin and Nutrition Research, 77(1), pp. 13-21, 2007.

* cited by examiner

*Primary Examiner* — Kahsay Habte
(74) *Attorney, Agent, or Firm* — Winstead PC

(57) ABSTRACT

The invention relates to iron(III) complex compounds and pharmaceutical compositions comprising them for the use as medicaments, in particular for the treatment and/or prophylaxis of iron deficiency symptoms and iron deficiency anemias.

10 Claims, No Drawings

FE(III)-PYRAZINE COMPLEX COMPOUNDS FOR TREATMENT AND PROPHYLAXIS OF IRON-DEFICIENCY PHENOMENA AND IRON-DEFICIENCY ANAEMIA

INTRODUCTION

The invention relates to iron(III)-pyrazine-2-ol-1-oxide complex compounds and pharmaceutical compositions comprising them for the use as medicaments, in particular for the treatment and/or prophylaxis of iron deficiency symptoms and iron deficiency anemias.

BACKGROUND

Iron is an essential trace element for almost all organisms and is relevant in particular with respect to growth and the formation of blood. The balance of the iron metabolism is in this case primarily regulated on the level of iron recovery from hemoglobin of ageing erythrocytes and the duodenal absorption of dietary iron. The released iron is taken up via the intestine, in particular via specific transport systems (DMT-1, ferroportin, transferrin, transferrin receptors), transferred into the circulation and thereby conveyed to the appropriate tissues and organs.

In the human body, the element iron is of great importance for oxygen transport, oxygen uptake, cell functions such as mitochondrial electron transport, and ultimately for the entire energy metabolism.

On average, the human body contains 4 to 5 g iron, with it being present in enzymes, in hemoglobin and myoglobin, as well as depot or reserve iron in the form of ferritin and hemosiderin.

Approximately half of this iron, about 2 g, is present as heme iron, bound in the hemoglobin of the erythrocytes. Since these erythrocytes have only a limited lifespan (75-150 days), new ones have to be formed constantly and old ones eliminated (over 2 million erythrocytes are being formed per second). This high regenerative capacity is achieved by macrophages phagocytizing the ageing erythrocytes, lysing them and thus recycling the iron thus obtained for the iron metabolism. The amount of iron of about 25 mg required daily for erythropoiesis is thus provided for the main part.

The daily iron requirement of an adult human is between 0.5 to 1.5 mg per day, infants and women during pregnancy require 2 to 5 mg of iron per day. The daily iron loss, e.g. by desquamation of skin and epithelial cells, is low; increased iron loss occurs, for example, during menstrual hemorrhage in women. Generally, blood loss can significantly reduce the iron level since about 1 mg iron is lost per 2 ml blood. In a healthy human adult, the normal daily loss of iron of about 1 mg is usually replaced via the daily food intake. The iron level is regulated by absorption, with the absorption rate of the iron present in food being between 6 and 12%; in the case of iron deficiency, the absorption rate is up to 25%. The absorption rate is regulated by the organism depending on the iron requirement and the size of the iron store. In the process, the human organism utilizes both divalent as well as trivalent iron ions. Usually, iron(III) compounds are dissolved in the stomach at a sufficiently acid pH value and thus made available for absorption. The absorption of the iron is carried out in the upper small intestine by mucosal cells. In the process, trivalent non-heme iron is first reduced in the intestinal cell membrane to Fe(II) for absorption, for example by ferric reductase (membrane-bound duodenal cytochrome b), so that it can then be transported into the intestinal cells by means of the transport protein DMT1 (divalent metal transporter 1). In contrast, heme iron enters the enterocytes through the cell membrane without any change. In the enterocytes, iron is either stored in ferritin as depot iron, or discharged into the blood by the transport protein ferroportin. Hepcidin plays a central role in this process because it is the most important regulating factor of iron uptake. The divalent iron transported into the blood by ferroportin is converted into trivalent iron by oxidases (ceruloplasmin, hephaestin), the trivalent iron then being transported to the relevant places in the organism by transferrin (see for example "Balancing acts: molecular control of mammalian iron metabolism". M. W. Hentze, *Cell* 117, 2004, 285-297.)

Mammalian organisms are unable to actively discharge iron. The iron metabolism is substantially controlled by hepcidin via the cellular release of iron from macrophages, hepatocytes and enterocytes.

In pathological cases, a reduced serum iron level leads to a reduced hemoglobin level, reduced erythrocyte production and thus to anemia.

External symptoms of anemias include fatigue, pallor as well as reduced capacity for concentration. The clinical symptoms of an anemia include low serum iron levels (hypoferremia), low hemoglobin levels, low hematocrit levels as well as a reduced number of erythrocytes, reduced reticulocytes and elevated levels of soluble transferrin receptors.

Iron deficiency symptoms or iron anemias are treated by supplying iron. In this case, iron substitution takes place either orally or by intravenous iron administration. Furthermore, in order to boost erythrocyte formation, erythropoietin and other erythropoiesis-stimulating substances can also be used in the treatment of anemias.

Anemia can often be traced back to malnutrition or low-iron diets or imbalanced nutritional habits low in iron. Moreover, anemias occur due to reduced or poor iron absorption, for example because of gastroectomies or diseases such as Crohn's disease. Moreover, iron deficiency can occur as a consequence of increased blood loss, such as because of an injury, strong menstrual bleeding or blood donation. Furthermore, an increased iron requirement in the growth phase of adolescents and children as well as in pregnant women is known. Since iron deficiency not only leads to a reduced erythrocyte formation, but thereby also to a poor oxygen supply of the organism, which can lead to the above-mentioned symptoms such as fatigue, pallor, reduced powers of concentration, and especially in adolescents, to long-term negative effects on cognitive development, a highly effective and well tolerated therapy is of particular interest.

Through using the Fe(III) complex compounds according to the invention, there is the possibility of treating iron deficiency symptoms and iron deficiency anemias effectively by oral application without having to accept the large potential for side effects of the classical preparations, the Fe(II) iron salts, such as $FeSO_4$, which is caused by oxidative stress. Poor compliance, which often is the reason for the deficient elimination of the iron deficiency condition, is thus avoided.

PRIOR ART

A multitude of iron complexes for the treatment of iron deficiency conditions is known from the prior art.

A very large proportion of these complex compounds consists of polymer structures. Most of these complex compounds are iron-polysaccharide complex compounds (WO20081455586, WO2007062546, WO20040437865, US2003236224, EP150085). It is precisely from this area that there are medicaments available on the market (such as Maltofer, Venofer, Ferinject, Dexferrum, Ferumoxytol).

Another large portion of the group of the polymer complex compounds is comprised of the iron-peptide complex compounds (CN101481404, EP939083, JP02083400).

There are also Fe complex compounds described in the literature that are structurally derived from macromolecules such as hemoglobin, chlorophyll, curcumin and heparin (US474670, CN1687089, Biometals, 2009, 22, 701-710).

Moreover, low-molecular Fe complex compounds are also described in the literature. A large number of these Fe complex compounds comprises carboxylic acid and amino acids as ligands. In this case, the focus is on aspartate (US2009035385) and citrate (EP308362) as ligands. Fe complex compounds containing derivatized phenylalanine groups as ligands are also described in this context (ES2044777).

Hydroxypyrone and hydroxypyridone Fe complex compounds are also described in the literature (EP159194, EP138420, EP107458, EP0120670). The corresponding 5-ring systems, the hydroxyfuranone Fe complex compounds, are also described in analogy thereto (WO2006037449). In particular, the hydroxypyridone Fe complex compounds, however, have comparatively low water solubility, making them less suitable, especially for oral administration. Furthermore the hydroxypyridone Fe complex compounds have comparatively low iron utilization.

INTERNATIONAL JOURNAL FOR VITAMIN AND NUTRITION RESEARCH, 77(1), 13-21 CODEN: IJVNAP; ISSN: 0300-9831, 2007 describes ferrichrysines for the use in the treatment of iron deficiency diseases.

Moreover, iron-cyclopentadienyl complex compounds are also described in the literature (GB842637).

Furthermore, 1-hydroxy-2(1H)-pyrazinone (HOPR—H) and 1-hydroxy-5,6-dimethyl-2(1H)-pyrazinone (HOPR-Me) have been described (Bull. Chem. Soc. Jpn., 66, 841-841 (1993); see also "Reviews On Heteroatom Chemistry", Vol. 18, 1998, page 87 to 118 and TETRAHEDRON, ELSEVIER SCIENCE PUBLISHERS, AMSTERDAM, NL, Vol. 51, No. 47, Nov. 20, 1995 (1995-11-20), pages 12995-13002 from the same authors). For the latter compound, the UV-vis spectrum of a 3:1 molar mixture with iron (III) is shown in an aqueous solution at various pH conditions. From the experiments the formation of 3:1-complexes with iron (III) is concluded. In contrast as to the pyrimidinones no possible structure of the pyrazinone-complex compounds is shown. An isolation of the iron complex compounds from the 3:1 mixtures in aqueous solution was not carried out. Accordingly, no solid iron complex compounds have been isolated or disclosed. Furthermore, the iron complex compounds are not proposed as medicaments, such as especially for the treatment of iron deficiency symptoms. The same authors suggest only the use of hexadentate 1-hydroxy-1H-pyrazine-2-one compounds as iron sequestering agents for treatment of iron overload conditions such as thalassemia (J. Org. Chem. 1997, 62, 3618-3624). By the administration of hydroxy-pyrimidinone or -pyrazine compounds to the body for the treatment of thalassemia iron might be removed—so no iron will be supplied—as in the treatment of iron deficiency anemia by administration of iron complex compounds in accordance with the present invention.

J. Am. Chem. Soc. 1985, 107, 6540-6546 describes tetradentate 1-hydroxy-1H-pyridine-2-one compounds as ligands and a binuclear iron complex compound therewith. The possibility to use the ligands for iron sequestering is mentioned, too. Similarly, Inorganica Chimica Acta, 135 (1987) 145-150 discloses the use of 1-hydroxy-1H-pyridine-2-ones as agents for masking iron.

NATURAL PRODUCT COMMUNICATIONS; 2011, 6(8), 1137-1140 and Journal of Agricultural and Food Chemistry, Jan. 1, 1981 (1981-01-01), pages 785-787 describe iron (III)-complexes of neoaspergillinic acid, wherein the first mentioned publication further generally mentions the antibacterial activity thereof. Chemical & Pharmaceutical Bulletin, Jan. 1, 1978 (1978-01-01), pages 1320-1322 describes structurally similar iron complex compounds. The use of such iron complexes as medicaments, such as especially in the treatment of iron deficiency anemia is not mentioned.

Chemical & Pharmaceutical Bulletin, Jan. 1, 1994 (1994-01-01), pages 277-279, Chemical & Pharmaceutical Bulletin, Jan. 1, 1981 (1981-01-01), pages 1510-1517 and HETEROCYCLES, ELSEVIER SCIENCE PUBLISHERS B.V. AMSTERDAM, NL, Vol. 35, No. 2, Jan. 1, 1993 (1993-01-01), pages 1279-1287 describe astechrome and its isolation as a metabolic product of Aspergillus strains. The use of such iron complexes as medicaments, such as especially in the treatment of iron deficiency anemia is not mentioned.

Iron salts (e.g. iron(II) sulfate, iron(II) fumarate, iron(III) chloride, iron(II) aspartate, iron(II) succinate) are another important constituent for the treatment of iron deficiency symptoms and iron deficiency anemias.

These iron salts are very problematic in that, in part, they are highly incompatible (up to 50%) in the form of nausea, vomiting, diarrhea and also obstipation and cramps. Moreover, free iron(II) ions which catalyze the formation (inter alia Fenton reaction) of reactive oxygen species (ROS) occur during the use of these iron(II) salts. These ROS cause damage to DNA, lipids, proteins and carbohydrates which has far-reaching effects in cells, tissue and organs. This complex of problems is known and, in the literature, is largely considered the cause for the high incompatibility and referred to as oxidative stress.

Therefore, iron(III)-1-hydroxy-1H-pyrazine-2-one or pyrazine-2-ol-1-oxide complex compounds, respectively, have not been described in the prior art neither as a medicament nor in particular for the use in the treatment and/or for prophylaxis of iron deficiency symptoms and iron deficiency anemia so far.

OBJECT

The object of the present invention lay in developing new therapeutically effective compounds that can be used for an effective therapy for the preferably oral treatment of iron deficiency symptoms and iron deficiency anemias. In this case, these iron complexes were supposed to exhibit significantly fewer side effects than the classically used Fe(II) salts. Furthermore, these iron complexes, in contrast to the known polymeric iron complex compounds, were, if possible, supposed to have a defined structure (stoichiometry) and be preparable by simple synthesis processes. In addition, the compounds should effect a high iron utilization rate upon oral administration, which is supported by a good water solubility. Finally, the iron complex compounds should have a very low toxicity and can be therefore administered in very high dosages. This goal was achieved by the development of novel Fe(III) complex compounds.

Furthermore, the novel iron complexes were supposed to be designed such that they are taken up into the intestinal cells directly via the membrane in order thus to release their complex-bound iron directly to the ferritin or the transferrin or to reach the bloodstream directly as an intact complex. Because of their properties, these new complexes are supposed to virtually not lead to the occurrence of high concentrations of free iron ions. For it is precisely the free iron ions that lead to the occurrence of ROS which are ultimately responsible for the side effects that occur.

In order to be able to meet these requirements, the inventors developed new Fe(III) complex compounds with a molecular weight that is not too large, medium lipophila and an optimal complex stability.

DESCRIPTION OF THE INVENTION

The inventors surprisingly found that Fe(III) complex compounds with pyrazine-2-ol 1-oxide were particularly suitable for the above-described requirements. It was possible to demonstrate that these Fe complex compounds exhibited a high iron uptake, whereby a quick therapeutic success in the treatment of iron deficiency anemia could be achieved. Especially in comparison to iron salts, the complex compounds according to the invention exhibited a faster and higher utilization. Furthermore, these new systems have significantly reduced side effects than the classically used iron salts since there is no noteworthy occurrence of free iron irons in this case. The complex compounds according to the invention exhibit almost no oxidative stress since there is no formation of free radicals. Thus, significantly fewer side effects occur in the case of these complex compounds than in the case of the Fe salts known from the prior art. The complex compounds exhibit good stability at various pH value ranges and comparably good solubility. Furthermore, the iron complex compounds have a very low toxicity and can therefore be administered in high dosages without side effects. Finally the complex compounds can be prepared well and are optimally suitable for the formulation of medicaments, in particular for oral administration.

Thus, the subject matter of the invention are iron(III)-pyrazine-2-ol-1-oxide complex compounds or their pharmaceutically acceptable salts for use as medicaments or synonymous for use in a method for therapeutic treatment of the human body, respectively.

The iron(III)-pyrazine-2-ol-1-oxide complex compounds as used in accordance with the present invention particularly include such compounds which comprise the following structural element:

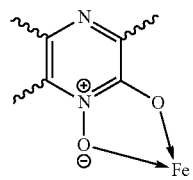

wherein ∿ respectively is a substituent of the ligand saturating the free valence and the arrows respectively represent coordinate bonds to the iron atom.

The terms
"pyrazine-2-ol-1-oxide",
"pyrazine-2-ol-1-oxide compounds" or
"pyrazine-2-ol-1-oxide-" ligands
according to the invention include the corresponding hydroxy starting compounds

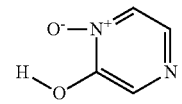

as well as the corresponding deprotonated ligands

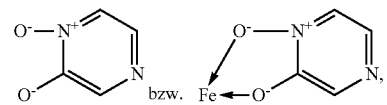

respectively
which are present in the corresponding iron(III) complex compounds.

Furthermore, according to the invention the aforementioned terms do not only comprise the respective base body:

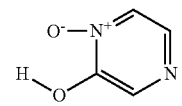

or the ligand compound resulting from deprotonating the underlying hydroxy compound

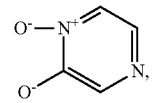

respectively
but as well their representatives substituted on the pyrimidine rings, resulting from the replacement of one or more hydrogen atoms on the pyrazine ring by other substituents. Accordingly, in context with the present invention the aforementioned terms refer to the entire class of "pyrazine-2-ol-1-oxide" compounds and the deprotonated ligands, including their representatives substituted on the pyrazine ring.

Formally, a (deprotonated) pyrazine-2-ol-1-oxide ligand according to the present invention carries a negative charge. This means, that in the case of three ligands per iron atom, the iron atom formally has the oxidation state +3. It is clear to the person skilled in the art that the shown formulas represent only one possible mesomeric formula and that there are several mesomeric formulas and that delocalisation of the electrons in the ligands or in the iron complex compound may be present, respectively, as shown hereinafter schematically.

In the iron(III) pyrazine-2-ol-1-oxide complex compounds according to the invention, the coordination number of the iron atoms is generally six (6), with a coordinating atoms generally being arranged octahedrally.

Furthermore, mono- or polynuclear iron(III) pyrazine-2-ol-1-oxide complex compounds in which one or more (such as 2, 3 or 4) iron atoms are present are also comprised according to the invention.

Generally, 1-4 iron atoms and 2-10 ligands can be present in the iron(III) pyrazine-2-ol-1-oxide complex compounds.

Mononuclear iron(III) pyrazine-2-ol-1-oxide complex compounds with at least one preferably tri-, preferably bidentate pyrazine-2-ol-1-oxide ligands are preferred. Mononuclear iron(III) pyrazine-2-ol-1-oxide complex compounds with one (1) central iron atom and three (3) pyrazine-2-ol-1-oxide ligands are particularly preferred.

The iron(III) pyrazine-2-ol-1-oxide complex compounds of the present invention are generally present in neutral form. However, salt like iron(III) pyrazine-2-ol-1-oxide complex compounds are also included, in which the complex has a positive or negative charge which is compensated, in particular, by pharmacologically compatible, substantially non-coordinating anions (such as, in particular, halogenides, such as chloride) or cations (such as, in particular, alkaline or alkaline-earth metal ions).

The iron(III) pyrazine-2-ol-1-oxide complex compounds according to the invention particularly include complex compounds, comprising at least one, preferably a bidentate pyrazine-2-ol-1-oxide ligand of the formula

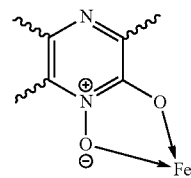

wherein ∿ respectively is a substituent saturating the free valence of the ligands, which can, as shown above, bond to one or even two different iron atoms in the sense of bridging.

Iron(III) pyrazine-2-ol-1-oxide complex compounds are preferred which exclusively comprise preferably bidentate pyrazine-2-ol-1-oxide ligands which may be the same or different. Furthermore, iron(III) pyrazine-2-ol-1-oxide complex compounds are particularly preferred which exclusively comprise the same pyrazine-2-ol-1-oxide ligands and very particularly preferred are tris(pyrazine-2-ol-1-oxide) iron(III) compounds.

Preferably, the molecular weight of the inventive iron (III)-pyrazine-2-ol 1-oxide-complex compounds is less than 1000 g/mol, more preferably less than 800 g/mol (each determined from the structural formula).

In a particularly preferred embodiment the iron(III) complex compounds according to the present invention comprise at least one, preferably three same or different, preferably same ligands of the formula (I):

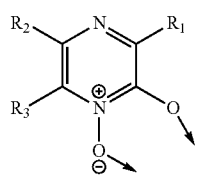

(I)

wherein
the arrows respectively represent a coordinate bond to one or different iron atoms, and
$R_1$, $R_2$, $R_3$ may be the same or different and are selected from the group consisting of:
hydrogen,
optionally substituted alkyl,
halogen,
optionally substituted alkoxy,
optionally substituted aryl,
optionally substituted alkoxycarbonyl, and
optionally substituted aminocarbonyl or
$R_2$ and $R_3$ together with the carbon atoms to which they are bonded, form an optionally substituted saturated or unsaturated 5- or 6-membered ring, which may optionally contain one or more heteroatoms, or pharmaceutically acceptable salts thereof.

The above-mentioned ring formation of the substituents $R_2$ and $R_3$ is schematically shown in the following formula:

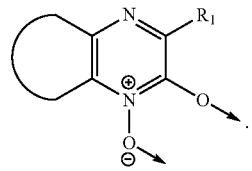

Therein, $R_1$ can have one of the mentioned meanings.

A preferred embodiment of the present invention relates to these iron(III) complex compounds containing at least one ligand of the formula (I):

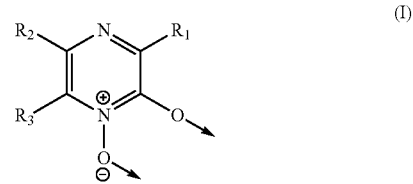

(I)

wherein
the arrows respectively represent a coordinate bond to one or different iron atoms, and
$R_1$, $R_2$, $R_3$ may be the same or different and are selected from the group consisting of:
hydrogen, and
optionally substituted alkyl.

Within the overall context of the invention, optionally substituted alkyl, in particular for the substituents $R_1$ to $R_3$, preferably includes:
straight-chained or branched alkyl with 1 to 8, preferably 1 to 6 carbon atoms, cycloalkyl with 3 to 8, preferably 5 or 6 carbon atoms, or alkyl with 1 to 4 carbon atoms, which is substituted with cycloalkyl, wherein these alkyl groups can be optionally substituted.

The above mentioned alkyl groups can be unsubstituted or substituted, preferably with 1 to 3 substituents. These substituents at the alkyl groups are preferably selected from the group consisting of: hydroxy, optionally substituted aryl, in particular as defined below, optionally substituted heteroaryl, in particular as defined below, optionally substituted alkoxy, in particular as defined below, optionally substituted alkoxycarbonyl, in particular as defined below, optionally substituted acyl, in particular as defined below, halogen, in particular as defined below, optionally substituted amino, in particular as defined below, optionally substituted aminocarbonyl, in particular as defined below, and cyano.

Halogen includes here and within the context of the present invention, fluorine, chlorine, bromine and iodine, preferably fluorine or chlorine.

In the above defined alkyl groups, optionally one or more, more preferably 1 to 3 carbon atoms can furthermore be replaced with hetero-analogous groups that contain nitrogen, oxygen or sulphur. This means, in particular, that, for example, one or more, preferably 1 to 3, still more preferred one (1) methylene group (—CH$_2$—) can be replaced in the alkyl groups by —NH—, —NR$_4$—, —O— or —S—, wherein R$_4$ is optionally substituted alkyl as defined above, preferably optionally substituted with 1 to 3 substituents, such as fluorine, chlorine, hydroxy or alkoxy, substituted C$_1$-C$_6$ alkyl, such as methyl or ethyl.

Examples of alkyl residues having 1 to 8 carbon atoms include: a methyl group, an ethyl group, an n-propyl group, an i-propyl group, an n-butyl group, an i-butyl group, a sec-butyl group, a t-butyl group, an n-pentyl group, an i-pentyl group, a sec-pentyl group, a t-pentyl group, a 2-methylbutyl group, a n-hexyl group, a 1-methylpentyl group, a 2-methylpentyl group, a 3-methylpentyl group, a 4-methylpentyl group, a 1-ethylbutyl group, a 2-ethylbutyl group, a 3-ethylbutyl group, a 1,1-dimethylbutyl group, a 2,2-dimethylbutyl group, a 3,3-dimethylbutyl group, a 1-ethyl-1-methylpropyl group, a n-heptyl group, a 1-methylhexyl group, a 2-methylhexyl group, a 3-methylhexyl group, a 4-methylhexyl group, a 5-methylhexyl group, a 1-ethylpentyl group, a 2-ethylpentyl group, a 3-ethylpentyl group, a 4-ethylpentyl group, a 1,1-dimethylpentyl group, a 2,2-dimethylpentyl group, a 3,3-dimethylpentyl group, a 4,4-dimethylpentyl group, a 1-propylbutyl group, an n-octyl group, a 1-methylheptyl group, a 2-methylheptyl group, a 3-methylheptyl group, a 4-methylheptyl group, a 5-methylheptyl group, a 6-methylheptyl group, a 1-ethylhexyl group, a 2-ethylhexyl group, a 3-ethylhexyl group, a 4-ethylhexyl group, a 5-ethylhexyl group, a 1,1-dimethylhexyl group, a 2,2-dimethylhexyl group, a 3,3-dimethylhexyl group, a 4,4-dimethylhexyl group, a 5,5-dimethylhexyl group, a 1-propylpentyl group, a 2-propylpentyl group, etc. Those with 1 to 6 carbon atoms are preferred. Methyl, ethyl, n-propyl, isopropyl, sec-butyl and n-butyl are most preferred.

Examples of alkyl groups produced by replacement with one or more hetero-analogous groups, such as —O—, —S—, —NH— or —N(R$_4$)— are preferably such groups in which one or more methylene groups (—CH$_2$—) are replaced with —O— while forming an ether group, such as methoxymethyl, ethoxymethyl, 2-methoxyethyl etc. Therefore, the definition of alkyl also includes, for example, alkoxyalkyl groups as defined below, which are produced from the above-mentioned alkyl groups by replacement of a methylene group with —O—. If, according to the invention, alkoxy group are additionally permitted as substituents of alkyl, several ether groups can also be formed in this manner (such as a —CH$_2$—O—CH$_2$—OCH$_3$-group). Thus, according to the invention, polyether groups are also comprised by the definition of alkyl.

Cycloalkyl groups with 3 to 8 carbon atoms preferably include: a cyclopropyl group, a cyclobutyl group, a cyclopentyl group, a cyclohexyl group, a cycloheptyl group, a cyclooctyl group, etc. A cyclopropyl group, a cyclobutyl group, a cyclopentyl group and a cyclohexyl group are preferred. The cycloalkyl groups may optionally be substituted preferably with 1 to 2 substituents such as hydroxyl or C$_1$-C$_6$ alkoxycarbonyl.

The definition of the optionally substituted alkyl also includes alkyl groups which are substituted by the above mentioned cycloalkyl groups, such as cyclopropylmethyl, cyclobutylmethyl, cyclopentylmethyl or cyclohexylmethyl.

Heterocyclic alkyl groups according to the invention are preferably those formed by the replacement of methylene with hetero-analogous groups from cycloalkyl, and include, for example, saturated 5 or 6-membered heterocyclic residues, which may be attached via a carbon atom or a nitrogen atom, and which preferably may have 1 to 3, preferably 2 heteroatoms, especially O, N, such as tetrahydrofuryl, azetidine-1-yl, substituted azetidinyl, such as 3-hydroxyazetidin-1-yl, pyrrolidinyl, such as pyrrolidin-1-yl, substituted pyrrolidinyl, such as 3-hydroxypyrrolidin-1-yl, 2-hydroxypyrrolidin-1-yl 2-methoxycarbonylpyrrolidin-1-yl, 2-ethoxycarbonylpyrrolidin-1-yl, 2-methoxypyrrolidin-1-yl, 2-ethoxypyrrolidin-1-yl, 3-methoxycarbonylpyrrolidin-1-yl, 3-ethoxycarbonylpyrrolidin-1-yl, 3-methoxypyrrolidin-1-yl, 3-ethoxypyrrolidine-1-yl, piperidinyl, such as piperidin-1-yl, piperidin-4-yl, substituted piperidinyl, such as 4-methyl-1-piperidyl, 4-hydroxy-1-piperidyl, 4-methoxy-1-piperidyl, 4-ethoxy-1-piperidyl, 4-methoxycarbonyl-1-piperidyl, 4-ethoxycarbonyl-1-piperidyl, 4-carboxy-1-piperidyl, 4-acetyl-1-piperidyl, 4-formyl-1-piperidyl, 1-methyl-4-piperidyl, 4-hydroxy-2,2,6,6-tetramethyl-1-piperidyl, 4-(dimethylamino)-1-piperidyl, 4-(diethylamino)-1-piperidyl, 4-amino-1-piperidyl, 2-(hydroxymethyl)-1-piperidyl, 3-(hydroxymethyl)-1-piperidyl, 4-(hydroxymethyl)-1-piperidyl, 2-hydroxy-1-piperidyl, 3-hydroxy-1-piperidyl, 4-hydroxy-1-piperidyl, morpholin-4-yl, substituted morpholinyl, such as 2,6-dimethyl morpholin-4-yl, piperazinyl, such as piperazin-1-yl, substituted piperazinyl, such as 4-methylpiperazin-1-yl, 4-ethylpiperazin-1-yl, 4-ethoxycarbonylpiperazin-1-yl, 4-methoxycarbonylpiperazin-1-yl, or tetrahydropyranyl, such as tetrahydropyran-4-yl, and which can optionally be condensated with aromatic rings, and which may optionally be substituted, such as with 1 to 2 substituents such as hydroxy, halogen, C$_1$-C$_6$-alkyl, etc. The definition of the optionally substituted alkyl groups thus includes also alkyl groups, which are substituted by the above-defined heterocyclic groups, such as 3-(1-piperidyl) propyl, 3-pyrrolidin-1-ylpropyl, 3-morpholinopropyl, 2-morpholinoethyl, 2-tetrahydropyran-4-ylethyl, 3-tetrahydropyran-4-ylpropyl, 3-(azetidin-1-yl) propyl etc.

Examples of a linear or branched alkyl group substituted with halogen and having 1 to 8, preferably 1 to 6 carbon atoms include, in particular: a fluoromethyl group, a difluoromethyl group, a trifluoromethyl group, a chloromethyl group, a dichloromethyl group, a trichloromethyl group, a bromomethyl group, a dibromomethyl group, a tribromomethyl group, a 1-fluoroethyl group, a 1-chloroethyl group, a 1-bromoethyl group, a 2-fluoroethyl group, a 2-chloroethyl group, a 2-bromoethyl group, a 1,2-difluoroethyl group, a 1,2-dichloroethyl group, a 1,2-dibromoethyl group, a 2,2,2-trifluoroethyl group, a heptafluoroethyl group, a 1-fluoropropyl group, a 1-chloropropyl group, a 1-bromopropyl group, a 2-fluoropropyl group, a 2-chloropropyl group, a 2-bromopropyl group, a 3-fluoropropyl group, a 3-chloropropyl group, a 3-bromopropyl group, a 1,2-difluoropropyl group, a 1,2-dichloropropyl group, a 1,2-dibromopropyl group, a 2,3-difluoropropyl group, a 2,3-dichloropropyl group, a 2,3-dibromopropyl group, a 3,3,3-trifluoropropyl group, a 2,2,3,3,3-pentafluoropropyl group, a 2-fluorobutyl group, a 2-chlorobutyl group, a 2-bromobutyl group, a 4-fluorobutyl group, a 4-chlorobutyl group, a 4-bromobutyl group, a 4,4,4-trifluorobutyl group, a 2,2,3,3,4,4,4-heptafluorobutyl group, a perfluorobutyl group, a 2-fluoropentyl group, a 2-chloropentyl group, a 2-bromopentyl group, a 5-fluoropentyl group, a 5-chloropentyl group, a 5-bromopentyl group, a perfluoropentyl group, a 2-fluorohexyl group, a 2-chlorohexyl group, a 2-bromohexyl group, a 6-fluorohexyl group, a 6-chlorohexyl group, a 6-bromohexyl group, a perfluorohexyl group, a 2-fluoroheptyl group, a 2-chloroheptyl group, a 2-bromoheptyl group, a 7-fluoroheptyl group, a 7-chloroheptyl group, a 7-bromoheptyl group, a perfluoroheptyl group, etc.

Examples of an alkyl group substituted with hydroxy include the above-mentioned alkyl residues, which have 1 to 3 hydroxy residues, such as, for example hydroxymethyl, 2-hydroxyethyl, 3-hydroxypropyl, 4-hydroxybutyl, 5-hydroxypentyl, 6-hydroxyhexyl.

Optionally substituted aryl preferably includes according to the invention aromatic hydrocarbon residues with 6 to 14 carbon atoms (with no hetero atom in the aromatic ring system), for example: phenyl, naphthyl, phenanthrenyl and anthracenyl. The aforementioned aromatic groups may be unsubstituted or substituted. In case of substitution, they preferably have one or more, preferably one (1) or two (2) substituents, in particular halogen, hydroxy, alkyl, alkoxy, in each case as explained above or below. A preferred aromatic group is phenyl. A preferred alkyl substituted with an aromatic group (arylalkyl) is benzyl.

Optionally substituted aryl according to the present invention further includes optionally substituted heteroaryl, that is, heteroaromatic groups, such as for example: pyridyl, pyridyl-N-oxide, pyrimidyl, pyridazinyl, pyrazinyl, thienyl, furyl, pyrrolyl, pyrazolyl, imidazolyl, thiazolyl, oxazolyl or isoxazolyl, indolizinyl, indolyl, benzo[b]thienyl, benzo[b] furyl, indazolyl, quinolyl, isoquinolyl, naphthyridinyl, quinazolinyl. 5- or 6-membered aromatic heterocycles such as, for example pyridyl, pyridyl-N-oxide, pyrimidyl, pyridazinyl, furyl and thienyl are preferred. The aforementioned heteroaromatic groups may be unsubstituted or substituted. In case of substitution, they preferably have one or more, preferably one (1) or two (2) substituents, in particular halogen, hydroxy, alkyl, alkoxy, in each case as explained above or below. Preferred examples of an alkyl substituted with a heteroaromatic group (hetarylalkyl) are methyl, ethyl, or propyl, in each case substituted with a heteroaromatic group, such as thienylmethyl, pyridylmethyl etc.

Optionally substituted alkoxy (RO—) is formally derived from the above mentioned optionally substituted alkyl residues by adding an oxygen atom and includes in context with the present invention, for example, linear or branched alkoxy groups with up to 6 carbon atoms, such as a methoxy group, an ethoxy group, an n-propyloxy group, an i-propyloxy group, an n-butyloxy group, an i-butyloxy group, a sec-butyloxy group, a t-butyloxy group, an n-pentyloxy group, an i-pentyloxy group, a sec-pentyloxy group, a t-pentyloxy group, a 2-methylbutoxy group, an n-hexyloxy group, an i-hexyloxy group, a t-hexyloxy group, a sec-hexyloxy group, a 2-methylpentyloxy group, a 3-methylpentyloxy group, a 1-ethylbutyloxy group, a 2-ethylbutyloxy group, a 1,1-dimethylbutyloxy group, a 2,2-dimethylbutyloxy group, a 3,3-dimethylbutyloxy group, a 1-ethyl-1-methylpropyloxy group, etc. A methoxy group, an ethoxy group, an n-propyloxy group, an i-propyloxy group, an n-butyloxy group, an i-butyloxy group, a sec-butyloxy group, a t-butyloxy group, etc., are preferred. The alkoxy groups may optionally be substituted, such as with the above possible substituents for alkyl.

Methoxy, ethoxy, n-propoxy, n-butoxy, etc. are preferred alkoxy.

Optionally substituted alkoxycarbonyl (RO—CO—) groups are formally derived from the above alkyl groups by adding a —O—C(O)— residue under formation of an optionally substituted alkyloxycarbonyl residue. In that regard reference can be made to the definition of the above-described alkyl groups. As an alternative optionally substituted alkoxycarbonyl (RO—CO—) groups are derived from the aforementioned alkoxy groups by the addition of a carbonyl group. Preferred alkoxycarbonyl groups comprise up to 6 carbon atoms and include for example: methoxycarbonyl, ethoxycarbonyl, n-propoxycarbonyl, n-butoxycarbonyl tert.-butoxycarbonyl etc., which may all be substituted as the above defined alkyl groups.

Optionally substituted amino carbonyl according to the invention can be formally derived from optionally substituted amino by adding a carbonyl residue ($(R)_2N-C(=O)-$). Therein optionally substituted amino preferably includes according to the invention: amino (—NH$_2$), optionally substituted mono- or dialkylamino (RHN—, $(R)_2N$—) for which with regard to the definition of optionally substituted alkyl reference can be made to the above definition. Furthermore included are optionally substituted mono- or diarylamino groups or mixed optionally substituted alkylarylamino groups, for which as regards the definition of optionally substituted alkyl or aryl reference can be made to the above definitions. Such groups include, for example methylamino, Dimethylamino, ethylamino, hydroxyethylamino, such as 2-hydroxyethlyamino, Diethylamino, phenylamino, methylphenylamino etc.

Optionally substituted amino further includes an optionally substituted cyclic amino, such as optionally substituted 5 or 6-membered cyclic amino that may contain further hetero atoms such as N, O, S, preferably O. Examples of such cyclic amino groups include the above-mentioned nitrogen-containing heterocyclic groups bonded through a nitrogen atom, such as piperidin-1-yl, 4-hydroxy-piperidin-1-yl, 2-(methoxycarbonyl)pyrrolidin-1-yl, pyrrolidin-1-yl, Morpholin-4-yl etc.

Examples of optionally substituted aminocarbonyl include therefore: Carbamoyl (H$_2$NC(=O)—), optionally substituted mono- or dialkylaminocarbonyl (RHNC(=O), $(R)_2$NC(=O)—), wherein reference can be made to the above definition of optionally substituted alkyl. Furthermore are included optionally substituted mono- or diarylaminocarbonyl residues or mixed, optionally substituted alkylarylaminocarbonyl residues, wherein reference can be made to the above definitions of optionally substituted alkyl or aryl. Preferred substituted aminocarbonyl groups comprise up to 14 carbon atoms. Such groups include for example methylaminocarbonyl, dimethylaminocarbonyl, ethylaminocarbonyl, diethylaminocarbonyl, phenylaminocarbonyl, diphenylaminocarbonyl, methylphenylaminocarbonyl etc.

Examples of the aforementioned ring formation of the substituents $R_2$ and $R_3$ as represented schematically by the following formula:

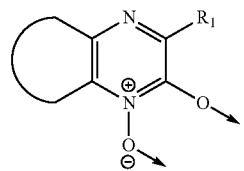

(wherein $R_1$ can have the mentioned meanings)

Include in particular:

compounds in which $R_2$ and $R_3$ together preferably represent a propylene (—CH$_2$—CH$_2$—CH$_2$—)— or a butylene (—CH$_2$—CH$_2$—CH$_2$—CH$_2$—) group, in which optionally one methylene group (—CH$_2$—) respectively can be replaced with —O—, —NH— or —NR$_4$—, wherein R$_4$ is defined as mentioned above and wherein the groups formed by R$_2$ and R$_3$ optionally can furthermore respectively be substituted by one to three substituents selected from the group consisting of hydroxy, oxo, C$_1$-C$_4$ alkoxy, amino and mono- or di-(C$_1$-C$_4$-alkyl)amino.

Exemplary ligands are the following:

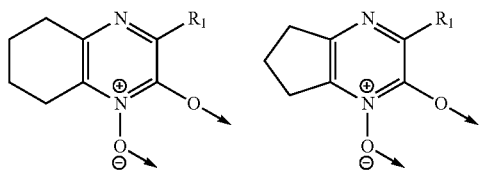

wherein $R_1$ respectively is as described above.

The iron(III) complex compounds of the formula (II) are particularly preferred:

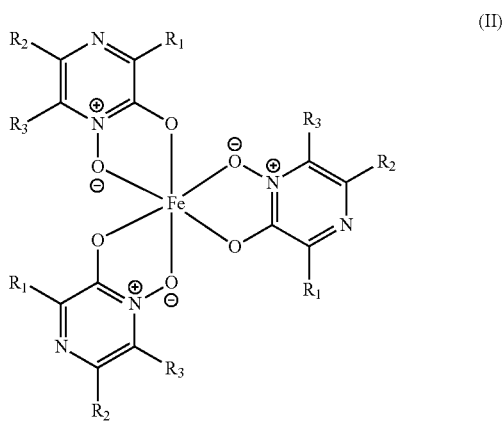

wherein $R_1$, $R_2$, and $R_3$ are each defined as above or preferably as defined below.

Furthermore, preferably $R_1$, $R_2$ and $R_3$ are the same or different and are selected from:
hydrogen,
$C_{1-6}$-alkyl, preferably as presented above, halogen, preferably as presented above,
$C_{3-6}$-cycloalkyl, preferably as presented above,
$C_{3-6}$-cycloalkyl-$C_{1-4}$-alkyl, preferably as presented above,
$C_{1-4}$-alkoxy-$C_{1-4}$-alkyl, preferably as presented above,
$C_{1-4}$-alkoxy-carbonyl, preferably as presented above,
$C_{1-4}$-mono-oder dialkylaminocarbonyl, preferably as presented above,
aminocarbonyl or carbamoyl ($H_2NCO$—), respectively hydroxy-$C_{1-4}$-alkyl, preferably as presented above, and halogen-$C_{1-4}$-alkyl, preferably as presented above;
or
$R_2$ and $R_3$ together with the carbon atoms to which they are bonded, form an optionally substituted saturated or unsaturated 5- or 6-membered ring, as explained above.

Particularly preferably $R_1$, $R_2$, and $R_3$ are the same or different and are selected from: hydrogen and $C_{1-6}$-alkyl, preferably as presented above, in particular hydrogen, methyl, ethyl and propyl, in particular i-propyl, butyl, especially sec-butyl. Most preferably, $R_1$, $R_2$ and $R_3$ are selected from: hydrogen, methyl and ethyl.

It is also particularly preferred, that $R_2$ and $R_3$ together with the carbon atoms to which they are bonded, form an optionally substituted saturated or unsaturated 5- or 6-membered ring, in particular an optionally substituted saturated 5- or 6-membered ring, particularly preferably a saturated 6-membered ring.

In a further embodiment of the invention there are provided the iron (III)-pyrazine-2-ol-1-oxide complex compounds in solid form. The term "solid form" means here in particular in contrast to the dissolved form, in which the iron (III)-pyrazine-2-ol-1-oxide complex compounds are present dissolved in a solvent such as water. The term "solid form" means also that the iron (III)-pyrazine-2-ol-1-oxide complex compounds at room temperature (23° C.) are present in solid form. The iron (III)-pyrazine-2-ol-1-oxide complex compounds can be present in an amorphous, crystalline or partially crystalline form. Also, the iron (III)-pyrazine-2-ol-1-oxide complex compounds of the invention may exist as hydrates.

It is clear to the person skilled in the art that the ligands according to the invention

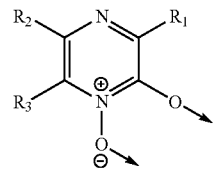

arise from the corresponding pyrazine-2-ol-1-oxide compounds:

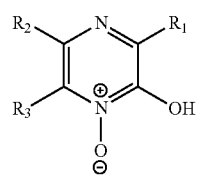

In the pyrazine-2-ol-1-oxide compounds there is a keto-enol-tautomerism between 1-hydroxypyrazine-2(1H) (IIIa) and pyrazine-2-ol-1-oxide (III), wherein the equilibrium state is determined by various factors.

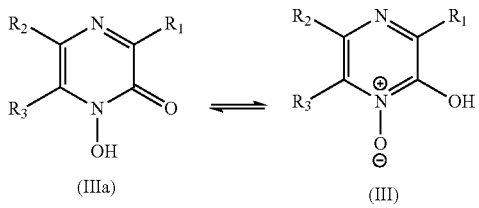

The ligand is formally obtained by cleavage of a proton from the corresponding pyrazine-1-oxide compounds (III):

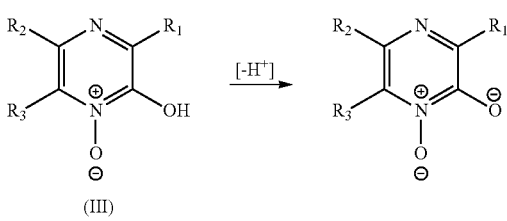

so formally carries a single negative charge.

Furthermore it is clear to a person skilled in the art that the pyrazine-2-ol-1-oxide compounds as used according to the present invention can be drawn by different notations (a and b), but both include the same issue of the N-oxide.

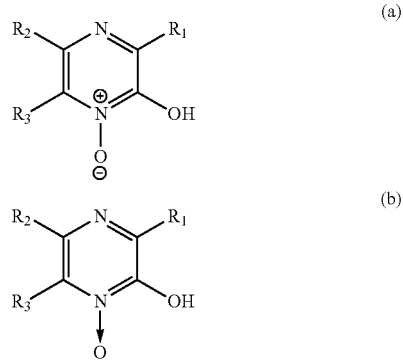

The same applies for the corresponding deprotonated form of the pyrazine-2-ol-1-oxide ligand compounds. Within the scope of the present invention all tautomeric forms are included, even if only one of the mesomeric formulas is drawn.

Depending on the substituent $R_1$, $R_2$, and $R_3$ they can also participate in the tautomeric resonance structures in the pyrazine-2-ol-1-oxide ligand and within the scope of the invention all such tautomers are included.

The iron(III) pyrazine-2-ol-oxide complex compounds of the present invention, in particular such as of the general formula (II) or the corresponding pyrazine-2-ol-1-oxide ligands, respectively, can be present in the form of various isomers or tautomers. Isomeric forms include, for example, regioisomers which differ in the position of the ligands relative to one another, including so-called optical isomers that have an image/mirror image relationship to one another. If asymmetric carbon atoms are present, the ligands can be present in the form of optical isomers which have an image/mirror image relationship to one another, and include pure enantiomers, mixtures of the enantiomers, in particular racemates. Enantiomerically pure ligands can be obtained, as is known to the person skilled in the art, by optical dissolution methods, such as reaction with chiral reagents to form diastereomers, separation of the diastereomers and release of the enantiomers.

Further preferred embodiments of the invention include:
(In the present invention, the digits 1-6 in "1-6C" or "01-6" or "1-4" in "1-4C" or "01-4" etc. in each case signify the number of the carbon atoms of the subsequent hydrocarbon group designations).

$R_1$, $R_2$ and $R_3$ are selected from the group consisting of:
  hydrogen,
  1-6C-alkyl, (this means alkyl with 1 to 6 carbon atoms),
  3-6C-cycloalkyl,
  3-6C-cycloalkyl-1-4C-alkyl,
  1-4C-alkoxy-1-4C-alkyl,
  hydroxy-1-4C-alkyl,
or $R_2$ and $R_3$ together form a propylene (—$CH_2$—$CH_2$—$CH_2$), butylene (—$CH_2$—$CH_2$—$CH_2$—$CH_2$—), azabutylene or oxabutylene group;
oder $R_2$ und $R_3$ bilden zusammen mit den Kohlenstoffen an die sie gebunden sind, ein ungesättigten Ring, der gegebenenfalls ein oder zwei weitere Heteroatome aufweisen kann, or pharmaceutically acceptable salts thereof.

Preferably, the aforementioned substituent groups are defined as follows:
1-6C-alkyl preferably includes straight-chained or branched alkyl groups with 1 to 6 carbon atoms. Examples therefore can be methyl, ethyl, n-propyl, iso-propyl, n-butyl, iso-butyl, sec-butyl, tert-butyl n-pentyl, iso-pentyl, neo-pentyl, n-hexyl, iso-hexyl and neo-hexyl.

3-6C-cycloalkyl preferably includes cycloalkyl 1 to 6 carbon atoms, such as cyclopropyl, cyclobutyl, cyclopentyl, cyclohexyl.

3-6C-cycloalkyl-1-4C-alkyl preferably includes a 1-6C-alkyl group described above, substituted with a 3-6C-cycloalkyl group described above. Examples therefor can be a cyclopropylmethyl, cyclopentylmethyl and cyclohexylmethyl group.

1-3C-alkoxy-carbonyl-1-6C-alkyl, preferably includes a 1-6C-alkyl group described above, which is linked to a carbonyl group which is present with a 1-3C alkoxy group as a carboxylic acid ester. Examples therefor can be methoxycarbonylmethyl, ethoxycarbonylmethyl, methoxycarbonylethyl, ethoxycarbonylethyl and isopropoxycarbonylmethyl.

1-4C-alkoxy preferably includes a 1-4C-alkoxy group, in which an oxygen atom is connected to a straight or branched alkyl chain with 1-4 carbon atoms. Examples of this group can be methoxy, ethoxy, propoxy and isobutoxy.

1-4C-alkoxy-1-4C-alkyl preferably includes a 1-4C-alkoxy group described above, which is substituted with a 1-4C-alkyl group described above. Examples of this group can be methoxyethyl, ethoxypropyl, methoxypropyl, isobutoxymethyl.

Hydroxy-1-4C-alkyl includes a 1-4C-alkyl group described above, which is substituted with a hydroxy group. Examples therefor can be hydroxyethyl, hydroxybutyl and hydroxyisopropyl.

Particularly preferred are:
$R_1$ $R_2$ and $R_3$ are selected from the group consisting of:
  hydrogen,
  1-6C-alkyl,
  1-4C-alkoxy-1-4C-alkyl,
  hydroxy-1-4C-alkyl;
or $R_2$ and $R_3$ together form a propylene (—$CH_2$—$CH_2$—$CH_2$), butylene (—$CH_2$—$CH_2$—$CH_2$—$CH_2$—), azabutylene or oxabutylene group;
or $R_2$ and $R_3$ together with the carbon atoms to which they are bonded form an unsaturated ring, which may contain further heteroatoms.

Particularly preferably:
$R_1$, $R_2$ and $R_3$ are selected from the group consisting of:
  hydrogen
  1-6C-alkyl;
  1-4C-alkoxy-1-4C-alkyl
or $R_2$ and $R_3$ together form a propylene (—$CH_2$—$CH_2$—$CH_2$) or butylene (—$CH_2$—$CH_2$—$CH_2$—$CH_2$—) group;
or $R_2$ and $R_3$ together with the carbona atoms to which they are bonded form an unsaturated ring, which may contain one further nitrogen atom.

Particularly preferred complex compounds of the general formula (II) are described in the examples.

The invention further relates to a method for the preparation of the iron(III) complex compounds according to the invention which comprises the reaction of a pyrazine-2-ol-1-oxide of formula (III) with an iron(III) salt.

Pyrazine-2-ol-1-oxides as the starting compounds include in particular those of the formula (III):

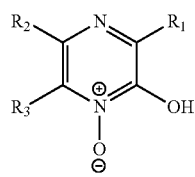

wherein $R_1$, $R_2$ and $R_3$ are defined as above, to the tautomeric resonance structures of which it has been referred to.

Examples of suitable iron(III) salts include: iron(III) chloride, iron(III) acetate, iron(III) sulfate, iron(III) nitrate and iron(III) acetylacetonate, among which iron(III) chloride is preferred.

A preferred method is shown in the following scheme:

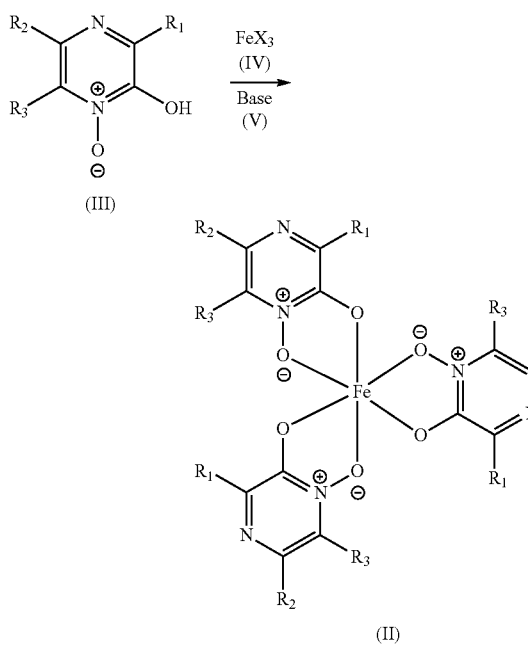

wherein $R_1$, $R_2$ and $R_3$ are as defined above, X is an anion such as halogenide, such as chloride, a carboxylate, such as acetate, sulphate, nitrate and acetylacetonate and base is a common organic or inorganic base.

In the method according to the invention, preferably 3 eq pyrazine-2-ol-1-oxide (III), using suitable iron(III) salts (IV) (in this case Fe(III) chloride, Fe(III) acetate, Fe(III) sulphate and Fe(III) acetylacetonate are particularly suitable), are reacted under standard conditions to form the corresponding complexes of the general formula (II). In this case, the synthesis is carried out under the pH conditions optimal for complex formation. The optimum pH value is set by adding a base (V); in this case, the use of sodium hydroxide, sodium carbonate, sodium hydrogen carbonate, sodium methanolate, potassium hydroxide, potassium carbonate, potassium hydrogen carbonate or potassium methanolate is particularly suitable.

The ligands (III) required for the preparation of the complexes where prepared according to the following synthesis method (J. Chem. Soc. 1949, 2707-2712). For this purpose, the commercially available or synthesized 2-aminohydroxamic acids (IV) were reacted under standard conditions with the commercially available or synthesized 1-2-dicarbonyl compounds of the general formula (V) to form ligands of the general formula (III). When using unsymmetrical 1-2-dicarbonyl compounds in this synthesis, this can result in the occurrence of the corresponding regioisomers (IIIa), which can be separated by standard methods which are well known to a person skilled in the art. For other substitution patterns of diketone (V) the reaction can also proceed largely regioselective, such as e.g. in the case of $R_2$=methyl, $R_3$=hydrogen.

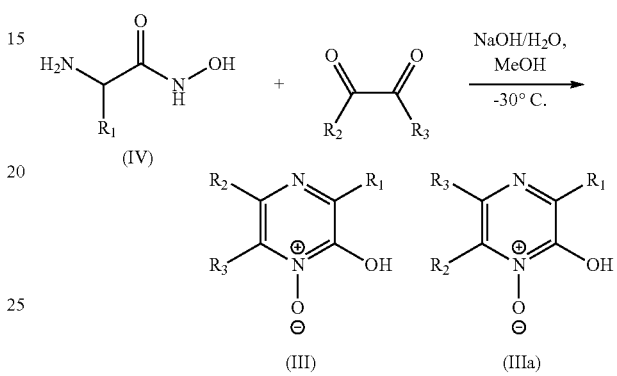

Analogously, it is also possible to use slightly modified synthesis routes under reactions conditions which are well know to a person skilled in the art, for the preparation of the respective ligands of the general formula (III). I. e., in the synthesis of Ohkanda et al. (Bull. Chem. Soc. Jpn. 1993, 66, 841-847) starting from the N-terminal protected amino acid of the general formula (VI) the corresponding O-benzyl protected amino hydroxamic acid (VII) can be prepared, which can be reacted to form the ligands of the general formula (III) after reaction with 1-2-dicarbonyl compounds of the general formula (IV) and cleavage of the O-benzyl group. In this alternative synthesis route it can come to the occurrence of (IIIa), too.

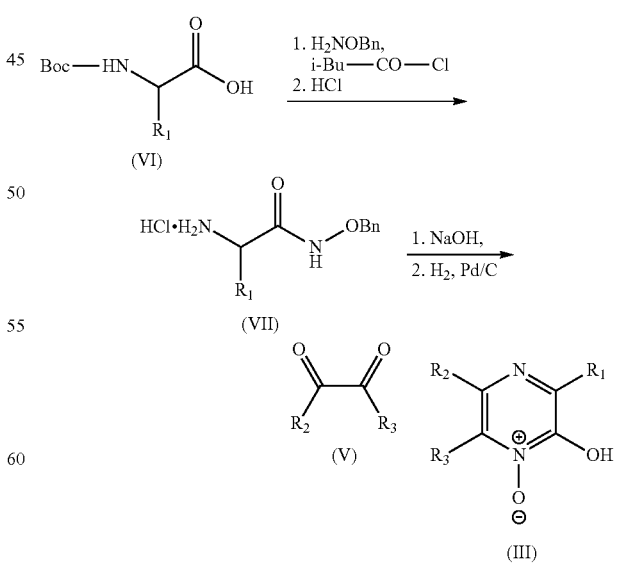

Boc = t-butyloxycarbonyl; Bn = benzyl

In general, the preparation of the pyrazine-2-ol-oxides (III) can be as well carried out by other synthesis routes familiar to a skilled person. Thus, for example, there is the possibility to react the respective substituted pyrazines (VIII) with suitable oxidizing agents, such as hydrogen peroxide or peroxycarboxylic acids, to form the desired products of general formula (III) (e.g. *J. Org. Chem.* 1958, 23, 1603-1606), wherein the region chemistry of the oxidation as well as the oxidation degree (simple or double) is determined by the reaction conditions, particularly the oxidizing agent and the substitution pattern of the corresponding pyrazines (e.g. *J. Heterocycl. Chem.* 1983, 19, 1061, J. Heterocycl. Chem. 1989, 26, 812).

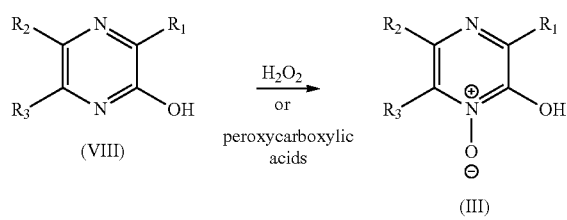

Examples of the pyrazine-2-ol-1-oxide starting compounds (III) include particularly the following:

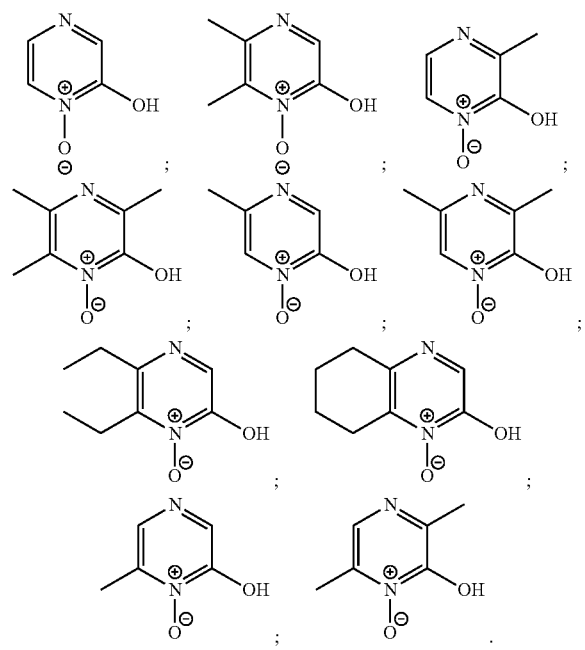

From these compounds the ligands of the iron complex compounds according to the present invention are derived by simple deprotonation at the hydroxy group.

Pharmaceutically acceptable salts of the compounds according to the invention in which the iron(III) complex formally carries a positive charge include, for example, salts with suitable anions, such as carboxylates, sulfonates, sulfates, chlorides, bromides, iodides, phosphates, tartrates, methane sulfonates, hydroxyethane sulfonates, glycinates, maleates, propionates, fumarates, toluene sulfonates, benzene sulfonates, trifluoroacetates, naphthalenedisulfonates-1,5, salicylates, benzoates, lactates, salts of malic acid, salts of 3-hydroxy-2-naphthoic acid-2, citrates and acetates.

Pharmaceutically acceptable salts of the compounds according to the invention in which the iron(III) complex formally carries a negative charge include, for example, salts with suitable pharmaceutically acceptable bases, such as, for example, salts with alkaline or alkaline-earth hydroxides, such as NaOH, KOH, $Ca(OH)_2$, $Mg(OH)_2$ etc., amine compounds such as ethylamine, diethylamine, triethylamine, ethyldiisopropylamine, ethanolamine, diethanolamine, triethanolamine, methylglucamine, dicyclohexylamine, dimethylaminoethanol, procaine, dibenzylamine, N-methylmorpholine, arginine, lysine, ethylenediamine, N-methylpiperidin, 2-amino-2-methyl-propanol-(1), 2-amino-2-methyl-propandiol-(1,3), 2-amino-2-hydroxylmethyl-propandiol-(1,3) (TRIS) etc.

The water-solubility or the solubility in physiological saline solution and thus, optionally, also the efficacy of the compounds according to the invention can be significantly influenced by salt formation in general, specifically by the choice of the counterion.

Preferably, the compounds according to the invention constitute neutral complex compounds.

Advantageous Pharmacological Effects:

Surprisingly, the inventors found that the iron(III) pyrazine-2-ol-1-oxide complex compounds which are the subject matter of the present invention and which are represented, in particular, by the general structural formula (II), are stable bioavailable iron complexes and suitable for use as a medicament for the treatment and prophylaxis of iron deficiency symptoms and iron deficiency anemias as well as the symptoms accompanying them.

The medicaments containing the compounds according to the invention are suitable for use in human and veterinary medicine.

The compounds according to the invention are thus also suitable for preparing a medicament for the treatment of patients suffering from symptoms of an iron deficiency anemia, such as, for example: fatigue, listlessness, lack of concentration, low cognitive efficiency, difficulties in finding the right words, forgetfulness, unnatural pallor, irritability, acceleration of heart rate (tachycardia), sore or swollen tongue, enlarged spleen, desire for strange foods (pica), headaches, lack of appetite, increased susceptibility to infections or depressive moods.

The iron(III) complex compounds according to the invention are furthermore suitable for the treatment of iron deficiency anemia in pregnant women, latent iron deficiency anemia in children and adolescents, iron deficiency anemia caused by gastrointestinal abnormalities, iron deficiency anemia due to blood loss, such as gastrointestinal hemorrhage (e.g. due to ulcers, carcinoma, hemorrhoids, inflammatory disorders, taking of acetylsalicylic acid), iron deficiency anemia caused by menstruation, iron deficiency anemia caused by injuries, iron deficiency anemia due to sprue, iron deficiency anemia due to reduced dietary iron uptake, in particular in selectively eating children and adolescents, immunodeficiency caused by iron deficiency anemia, brain function impairment caused by iron deficiency anemias, restless leg syndrome caused by iron deficiency anemias, iron deficiency anemias in the case of cancer, iron deficiency anemias caused by chemotherapies, iron deficiency anemias triggered by inflammation (AI), iron deficiency anemias in the case of congestive cardiac insufficiency (CHF; congestive heart failure), iron deficiency anemias in the case of chronic renal insufficiency stage 3-5 (CKD 3-5; chronic kidney diseases stage 3-5), iron deficiency anemias triggered by chronic inflammation (ACD), iron deficiency anemias in the case of rheumatoid arthritis (RA), iron deficiency anemias in the case of systemic lupus erythematosus (SLE) and iron deficiency anemias in the case of inflammatory bowel diseases (IBD).

Administration can take place over a period of several months until the iron status is improved, which is reflected, for example, by the hemoglobin level, transferrin saturation and the serum ferritin level of the patients, or until the desired improvement of the state of health affected by iron deficiency anemia. The preparation according to the invention can be taken by children, adolescents and adults.

The applied compounds according to the invention can in this case be administered both orally as well as parentally. Oral administration is preferred.

The compounds according to the invention and the aforementioned combinations of the compounds according to the invention with other active substances or medicines can thus be used, in particular, for the preparation of medicaments for the treatment of iron deficiency anemia, such as iron deficiency anemia in pregnant women, latent iron deficiency anemia in children and adolescents, iron deficiency anemia caused by gastrointestinal abnormalities, iron deficiency anemia due to blood loss, such as gastrointestinal hemorrhage (e.g. due to ulcers, carcinoma, hemorrhoids, inflammatory disorders, taking of acetylsalicylic acid), menstruation, injuries, iron deficiency anemia due to sprue, iron deficiency anemia due to reduced dietary iron uptake, in particular in selectively eating children and adolescents, immunodeficiency caused by iron deficiency anemia, brain function impairment caused by iron deficiency anemia, restless leg syndrome.

The application according to the invention leads to an improvement of the iron, hemoglobin, ferritin and transferrin levels, which, in particular in children and adolescents, but also in adults, is accompanied by an improvement in short-term memory tests (STM), long-term memory tests (LTM), Ravens' progressive matrices test, in the Wechsler adult intelligence scale (WAIS) and/or in the emotional coefficient (Baron EQ-i, YV test, youth version), or to an improvement of the neutrophile level, the antibody levels and/or lymphocyte function.

Furthermore, the present invention relates to pharmaceutical compositions comprising one or more of the compounds according to the invention, in particular according to the formula (II), as well as optionally one or more further pharmaceutically effective compounds, as well as optionally one or more pharmacologically acceptable carriers and/or auxiliary substances and/or solvents. The said pharmaceutical compositions contain, for example up to 99 weight-% or up to 90 weight-% or up to 80 weight-% or or up to 70 weight-% of the compounds of the invention, the remainder being each formed by pharmacologically acceptable carriers and/or auxiliaries and/or solvents.

These are common pharmaceutical carriers, auxiliary substances or solvents. The above-mentioned pharmaceutical compositions are suitable, for example, for intravenous, intraperitoneal, intramuscular, intravaginal, intrabuccal, percutaneous, subcutaneous, mucocutaneous, oral, rectal, transdermal, topical, intradermal, intragasteral or intracutaneous application and are provided, for example, in the form of pills, tablets, enteric-coated tablets, film tablets, layer tablets, sustained release formulations for oral, subcutaneous or cutaneous administration (in particular as a plaster), depot formulations, dragees, suppositories, gels, salves, syrup, granulates, suppositories, emulsions, dispersions, microcapsules, microformulations, nanoformulations, liposomal formulations, capsules, enteric-coated capsules, powders, inhalation powders, microcrystalline formulations, inhalation sprays, epipastics, drops, nose drops, nose sprays, aerosols, ampoules, solutions, juices, suspensions, infusion solutions or injection solutions etc.

Preferably, the compounds according to the invention as well as pharmaceutical compositions containing such compounds are applied orally, although other forms, such as parentally, in particular intravenously, are also possible.

For this purpose, the compounds according to the invention are preferably provided in pharmaceutical compositions in the form of pills, tablets, enteric-coated tablets, film tablets, layer tablets, sustained release formulations for oral administration, depot formulations, dragees, granulates, emulsions, dispersions, microcapsules, microformulations, nanoformulations, liposomal formulations, capsules, enteric-coated capsules, powders, microcrystalline formulations, epipastics, drops, ampoules, solutions, suspensions, infusion solutions or injection solutions.

In a preferred embodiment of the invention the iron complex compounds are administered in the form of a tablet or capsule. These can for example be present as acid-resistant forms or with pH-dependent coatings.

The compounds according to the invention can be administered in pharmaceutical compositions which may contain various organic or inorganic carrier and/or auxiliary materials as they are customarily used for pharmaceutical purposes, in particular for solid medicament formulations, such as, for example, excipients (such as saccharose, starch, mannitol, sorbitol, lactose, glucose, cellulose, talcum, calcium phosphate, calcium carbonate), binding agents (such as cellulose, methylcellulose, hydroxypropylcellulose, polypropyl pyrrolidone, gelatine, gum arabic, polyethylene glycol, saccharose, starch), disintegrating agents (such as starch, hydrolyzed starch, carboxymethylcellulose, calcium salt of carboxymethylcellulose, hydroxypropyl starch, sodium glycol starch, sodium bicarbonate, calcium phosphate, calcium citrate), lubricants (such as magnesium stearate, talcum, sodium laurylsulfate), a flavorant (such as citric acid, menthol, glycin, orange powder), preserving agents (such as sodium benzoate, sodium bisulfite, methylparaben, proylparaben), stabilizers (such as citric acid, sodium citrate, acetic acid and multicarboxylic acids from the titriplex series, such as, for example, diethylenetriaminepentaacetic acid (DTPA), suspending agents (such as methycellulose, polyvinyl pyrrolidone, aluminum stearate), dispersing agents, diluting agents (such as water, organic solvents), beeswax, cocoa butter, polyethylene glycol, white petrolatum, etc.

Liquid medicament formulations, such as solvents, suspensions and gels usually contain a liquid carrier, such as water and/or pharmaceutically acceptable organic solvents. Furthermore, such liquid formulations can also contain pH-adjusting agents, emulsifiers or dispersing agents, buffering agents, preserving agents, wetting agents, gelatinizing agents (for example methylcellulose), dyes and/or flavouring agents. The compositions may be isotonic, that is, they can have the same osmotic pressure as blood. The isotonicity of the composition can be adjusted by using sodium chloride and other pharmaceutically acceptable agents, such as, for example, dextrose, maltose, boric acid, sodium tartrate, propylene glycol and other inorganic or organic soluble substances. The viscosity of the liquid compositions can be adjusted by means of a pharmaceutically acceptable thickening agent, such as methylcellulose. Other suitable thickening agents include, for example, xanthan gum, carboxymethylcellulose, hydroxypropylcellulose, carbomer and the like. The preferred concentration of the thickening agent will depend on the agent selected. Pharmaceutically acceptable preserving agents can be used in order to increase the storage life of the liquid composition. Benzyl alcohol can be suitable, even though a plurality of preserving agents including, for example, paraben, thimerosal, chlorobutanol and benzalkonium chloride can also be used.

The active substance can be administered, for example, with a unit dose of 0.001 mg/kg to 500 mg/kg body weight, for example 1 to 4 times a day. However, the dose can be increased or reduced depending on the age, weight, condition of the patient, severity of the disease or type of administration.

EXAMPLES

The designation of the ligands has been carried according to the IUPAC nomenclature with the program ACD/name, version 12.01 according to Advanced Chemistry Development Inc.

| Abbreviations | | | |
|---|---|---|---|
| s | singlet | t | triplet |
| d | doublet | q | quartet |
| dd | double doublet | m | multiplet (broad/superimposed) |
| L | ligand | | |

Starting Compounds:

A. Pyrazine-2-ol 1-oxide

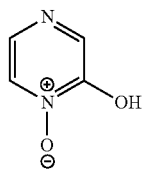

The synthesis has been carried out in analogy to the following literature: G. Dunn et al., *J. Chem. Soc.* 1949, 2707-2712.

B. 5,6-Dimethyl-pyrazine-2-ol 1-oxide

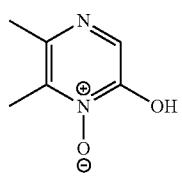

The synthesis has been carried out in analogy to the following literature: G. Dunn et al., *J. Chem. Soc.* 1949, 2707-2712.

C. 3-Methylpyrazine-2-ol-1-oxide

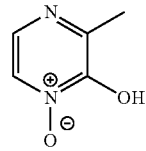

The synthesis has been carried out in analogy to the following literature: G. Dunn et al., *J. Chem. Soc.* 1949, 2707-2712.

D. 3,5,6-Trimethylpyrazine-2-ol-1-oxide

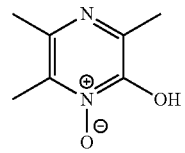

The synthesis has been carried out in analogy to the following literature: G. Dunn et al., *J. Chem. Soc.* 1949, 2707-2712.

E. 5-Methylpyrazine-2-ol-1-oxide

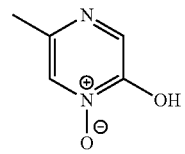

100 mmol (9 g) glycine hydroxamic acid were cooled to −25° C. in 200 ml water and methanol each, 100 mmol (15.4 ml 40% solution) methylglyoxal were added dropwise and subsequently the pH was adjusted to approximately pH 11 with 10 ml 30% NaOH. Heating up to 5° C. was carried out in 2 h and concentrated under vacuum to half of the solvent volume. A pH 3 was adjusted with 20% HCl, precipitated solid was filtered off and dried. 7.28 g (52% yield) of the title compound were obtained.

IR (in substance, cm$^{-1}$): 1644, 1577, 1527, 1454, 1425, 1381, 1333, 1229, 1141, 1062, 1028, 949, 896, 835, 806, 732.

CHN-elementary analysis: C, 42.91; H, 4.49; N, 19.54.

1H-NMR (DMSO-d$_6$, 400 MHz): δ [ppm]=8.04 (s, 1H), 7.83 (s, 1H), 2.21 (s, 3H).

F. 3,5-Dimethylpyrazine-2-ol-1-oxide

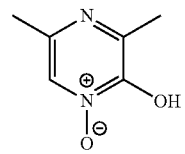

407 mmol (42.4 g) alanine hydroxamic acid were cooled to −10° C. in 200 ml water and methanol each, 400 mmol (57 ml 40% solution) methylglyoxal were added dropwise and subsequently the pH was adjusted to approximately pH 11 with 19 ml 30% NaOH. Heating up to 0° C. was carried out within 2 h and then pH 3 was adjusted with 20% NaOH. The solution was concentrated until dryness under vacuum distillation, the residue was heated to reflux with 50 ml ethanol, after cooling filtering was carried out and the filtrate again concentrated until dryness. 44 g of the solid residue were dissolved in 50 ml water and 15 mmol (4.06 g) $FeCl_3*6H_2O$ were added, heated up to 50° C. for 30 minutes, concentrated and stored at 5° C. for 4 h. The precipitated solid was filtered off and dried. 3.7 g solid in 50 ml water and 10 ml ethanol were adjusted to pH 11 with 6 ml 1 M NaOH, stirred over night and centrifugalized. The supernatant was decanted, pH 3 was adjusted with 3 ml 1 M HCl and concentrated until dryness. 4.2 g solid were refluxed in 20 ml ethanol, cooled and filtered off. The filtrate was again concentrated until dryness and the obtained 2.8 g solid were suspended with 10 ml water, heated up to 50° C. and left for cooling over night. The suspension was centrifugalized, the supernatant decanted and concentrated until dryness. 2.0 g (3.5% yield) of the title compound were obtained.

IR (in substance, $cm^{-1}$): 1633, 1579, 1526, 1423, 1372, 1318, 1274, 1212, 1148, 1030, 987, 934, 829, 751, 681, 613.

LC-MS (m/z): 141.6 (M+H).

CHN-elementary analysis: C, 50.15; H, 5.75; N, 18.83.

1H-NMR (DMSO-$d_6$, 400 MHz): δ [ppm]=7.64 (s, 1H), 2.31 (s, 3H), 2.15 (s, 3H).

G. 5,6-Diethylpyrazine-2-ol-1-oxide

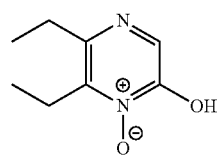

The synthesis has been carried out in analogy to the following literature: G. Dunn et al., *J. Chem. Soc.* 1949, 2707-2712.

H. 5,6,7,8-Tetrahydroquinoxaline-2-ol-1-oxide

The synthesis has been carried out in analogy to the following literature: G. Dunn et al., *J. Chem. Soc.* 1949, 2707-2712.

I. 6-Methylpyrazine-2-ol-1-oxide

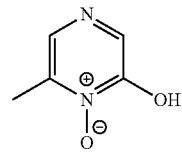

156 mmol (20 g) 2-chloro-6-methylpyrazine were dissolved in 80 ml 96% sulfuric acid, 222 mmol (63 g) potassium peroxodisulfate were added portion wise at 10° C. and stirring was carried out for 2 days at 10° C. and 1 day at room temperature (see also C. E. Mixan, R. Garth, *J. Org. Chem.* 1977, 42, 1869-1871). The reaction mixture was poured on 200 g ice, under addition of ethanol neutralization was carried out with calcium hydroxide, then filtered off and washed with ethanol. The filtrate was evaporated until dryness, the obtained solid (20 g) were refluxed in 300 ml 20% KOH solution for 3 h and after cooling pH 3 was adjusted with 20% HCl. The solution was evaporated until dryness, the residue boiled with 0.2 l ethanol under reflux for 2 h, after cooling filtered and the filtrate evaporated until dryness. After recrystallization from ethanol/tetrahydrofuran from 7.4 g raw product 2.17 g (10% yield, 93% purity) of the title compound were obtained.

IR (in substance, $cm^{-1}$): 1649, 1573, 1541, 1454, 1413, 1389, 1374, 1297, 1247, 1208, 1171, 1126, 1055, 1037, 981, 896, 848, 816, 718.

LC-MS (m/z): 127.4 (M+H).

CHN-elementary analysis: C, 44.77; H, 4.56; N, 20.72.

1H-NMR (DMSO-$d_6$, 400 MHz): δ [ppm]=7.95 (s, 1H), 7.30 (s, 1H), 2.31 (s, 3H).

J. 3,6-Dimethylpyrazine-2-ol-1-oxide

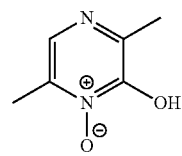

The synthesis has been carried out in analogy to the following literature: A. Ohta et al., *J. Heterocyclic Chem.* 1981, 18, 555-558.

Iron Complex Compounds

EXAMPLES

Example 1

Tris-(pyrazine-2-ol 1-oxide)iron(III)-complex

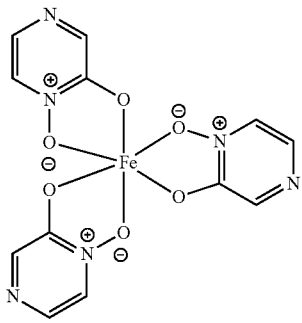

15 mmol (1.77 g) pyrazine-2-ol-1-oxide (in analogy to G. Dunn et al., *J. Chem. Soc.* 1949, 2707-2712) were dissolved in 50 ml ethanol, heated to reflux and 5 mmol (1.352 g) FeCl$_3$*6H$_2$O dissolved in 20 ml ethanol were added. Under reflux 50 ml water were added dropwise and the reaction mixture was left for cooling. Subsequently pH 4.5 was adjusted with 15 ml 1 M NaOH, stirred at 50° C. for 2 h and after cooling the product was filtered off and dried in a vacuum drying oven at 50° C. 1.89 g (95% Fe-yield) of the title compound were obtained.

IR (in substance, cm$^{-1}$): 3096, 3060, 1595, 1517, 1476, 1440, 1340, 1289, 1188, 1157, 1048, 921, 890, 830, 801.
Fe-content: 13.8% [m/m]
chloride-content: 3.0% [m/m]

Example 2

Tris-(5,6-dimethyl pyrazine-2-ol 1-oxide)iron(III)-complex

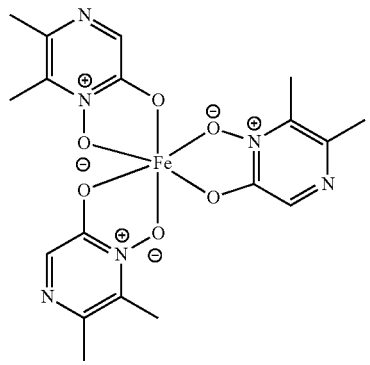

15 mmol (2.213 g) 5,6-dimethylpyrazine-2-ol 1-oxide (in analogy to G. Dunn et al., *J. Chem. Soc.* 1949, 2707-2712) were dissolved in 50 ml ethanol, heated to reflux and 5 mmol (1.352 g) FeCl$_3$*6H$_2$O dissolved in 25 ml ethanol were added. Under reflux 75 ml water were added dropwise and the reaction mixture was left for cooling. Subsequently pH 4.5 was adjusted with 10 ml 1 M NaOH, stirred at 50° C. for 2 h and after cooling the product was filtered off and dried in a vacuum drying oven at 50° C. 2.07 g (86% Fe-yield) of the title compound were obtained.

IR (in substance, cm$^{-1}$): 3037, 1594, 1477, 1361, 1276, 1217, 1161, 1093, 1065, 1018, 968, 878, 771, 692.
Fe-content: 11.63% [m/m]
chloride-content: 0.0% [m/m] (not detectable)

Example 3

Tris-(3-methylpyrazine-2-ol-1-oxide)iron(III)-complex

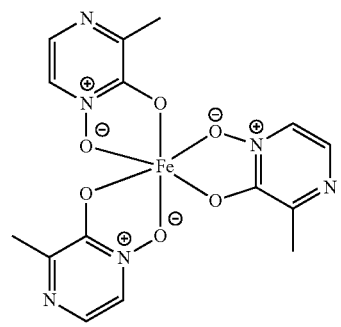

12 mmol (1.51 g) 3-methylpyrazine-2-ol-1-oxide (in analogy to G. Dunn et al., *J. Chem. Soc.* 1949, 2707-2712) were heated to reflux in 100 ml ethanol and 4 mmol (1.08 g) FeCl$_3$*6H$_2$O dissolved in 20 ml ethanol were added. Under reflux 120 ml water were added dropwise, half of the solvent were distilled off and the reaction mixture was left for cooling. Subsequently pH was adjusted to 4.4 with 9 ml 1 M NaOH and stirred for 15 min at 50° C. After cooling the product was filtered off and dried. 1.57 g (89% Fe-yield) of the title compound were obtained.

IR (in substance, cm$^{-1}$): 1588, 1523, 1487, 1373, 1333, 1314, 1257, 1185, 1099, 1032, 946, 881, 809, 793, 752, 729.
CHN-elementary analysis: C, 41.92; H, 3.58; N, 19.33.
Fe-content: 12.7% [m/m]
chloride-content: 0.0% [m/m] (not detectable)

Example 4

Tris-(3,5,6-trimethylpyrazine-2-ol-1-oxide)iron(III)-complex

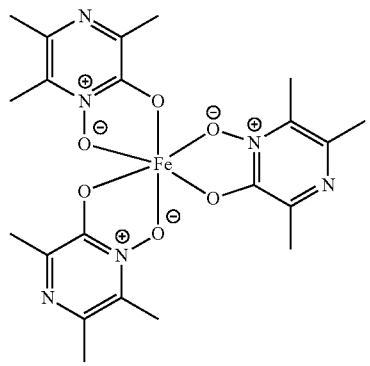

39 mmol (6.0 g) 3,5,6-trimethylpyrazine-2-ol-1-oxide (in analogy to G. Dunn et al., *J. Chem. Soc.* 1949, 2707-2712) were heated to reflux in 80 ml ethanol and 13 mmol (3.5 g) FeCl$_3$*6H$_2$O dissolved in 10 ml ethanol were added. Under reflux 80 ml water were added dropwise, half of the solvent was distilled off and the reaction mixture was left for cooling. Subsequently pH 4.4 was adjusted with 48 ml 1 M NaOH and stirred for 15 min at 50° C. After cooling the product was filtered off and dried. 6.48 g (90% Fe-yield) of the title compound were obtained.

IR (in substance, cm$^{-1}$): 1587, 1486, 1413, 1363, 1332, 1182, 1129, 1082, 1005, 940, 873, 749, 721.

CHN-elementary analysis: C, 47.67; H, 5.26; N, 15.82.

Fe-content: 10.07% [m/m]

chloride-content: 0.0% [m/m] (not detectable)

Example 5

Tris-(5-methylpyrazine-2-ol-1-oxide)iron(III)-complex

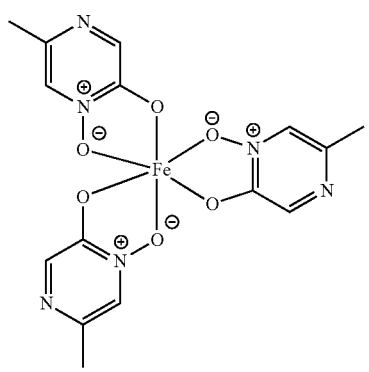

42.8 mmol (6.0 g, 90% purity) 5-methylpyrazine-2-ol-1-oxide were heated to reflux in 360 ml ethanol and 14.3 mmol (3.86 g) FeCl$_3$*6H$_2$O dissolved in 20 ml ethanol were added. Under reflux 380 ml water were added dropwise, half of the solvent was distilled off and the reaction mixture was left for cooling. Subsequently pH 4.4 was adjusted with 45 ml 1 M NaOH and stirred for 30 min at 50° C. After cooling the product was filtered off and dried. 5.31 g (80% Fe-yield) of the title compound were obtained.

IR (in substance, cm$^{-1}$): 1611, 1514, 1486, 1450, 1398, 1380, 1340, 1256, 1205, 1184, 1122, 1039, 1007, 939, 918, 873, 840, 757, 742.

CHN-elementary analysis: C, 40.88; H, 3.55; N, 18.86.

Fe-content: 11.96% [m/m]

chloride-content: 0% [m/m] (not detectable)

Example 6

Tris-(3,5-dimethylpyrazine-2-ol-1-oxide)-iron(III)-complex

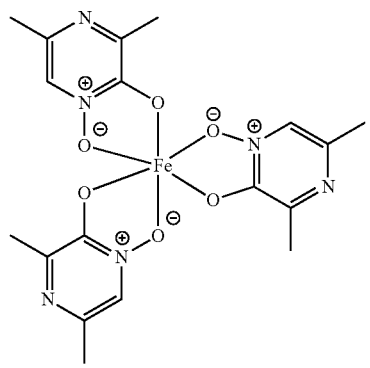

11.4 mmol (1.68 g) 3,5-dimethylpyrazine-2-ol-1-oxide were heated to reflux in 50 ml ethanol and 3.8 mmol (1.03 g) FeCl$_3$*6H$_2$O dissolved in 10 ml ethanol were added, under reflux 50 ml water were added dropwise, half of the solvent was distilled off and the reaction mixture was left for cooling. Subsequently pH 4.4 was adjusted with 7 ml 1 M NaOH and after distillation of further 30 ml solvent stirred over night. The product was filtered off and dried, 1.11 g (47% Fe-yield) of the title compound were obtained.

IR (in substance, cm$^{-1}$): 1526, 1489, 1373, 1332, 1306, 1226, 1141, 1055, 940, 834, 748, 643, 605.

Fe-content: 9.07% [m/m]

chloride-content: 0.79% [m/m]

Example 7

Tris-(5,6-diethylpyrazine-2-ol-1-oxide)iron(III)-complex

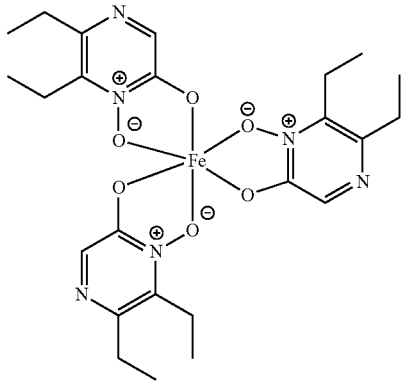

6.6 mmol (1.1 g) 5,6-diethylpyrazine-2-ol-1-oxide were heated to reflux in 30 ml ethanol and 2.2 mmol (0.6 g) FeCl$_3$*6H$_2$O dissolved in 10 ml ethanol were added. Under reflux 35 ml water were added dropwise, half of the solvent was distilled off and the reaction mixture was left for cooling. Subsequently pH 4.2 was adjusted with 3.8 ml 1 M NaOH, the product was filtered off and dried. 1.15 g (99% Fe-yield) of the title compound were obtained.

IR (in substance, cm$^{-1}$): 2974, 2937, 2876, 1706, 1588, 1509, 1479, 1457, 1353, 1260, 1214, 1158, 1105, 1048, 981, 950, 895, 782, 754, 687, 667, 608.

CHN-elementary analysis: C, 51.5; H, 6.27; N, 14.31.
Fe-content: 10.6% [m/m]
chloride-content: 3.4% [m/m]

Example 8

Tris-(5,6,7,8-tetrahydroquinoxaline-2-ol-1-oxide)-iron(III)-complex

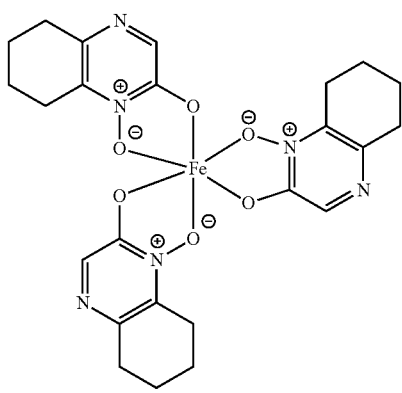

15 mmol (2.62 g) 5,6,7,8-tetrahydroquinoxaline-2-ol-1-oxide were heated to reflux in 100 ml ethanol and 5 mmol (1.35 g) FeCl$_3$*6H$_2$O dissolved in 30 ml ethanol were added. Under reflux 100 ml water were added dropwise, half of the solvent was distilled off and the reaction mixture was left for cooling. Subsequently pH 4.5 was adjusted with 15 ml 1 M NaOH, the product was filtered off and dried. 2.52 g (91% Fe-yield) of the title compound were obtained.

IR (in substance, cm$^{-1}$): 2933, 1592, 1519, 1486, 1433, 1366, 1325, 1266, 1245, 1217, 1184, 1134, 1102, 1067, 987, 966, 887, 856, 821, 762, 690, 633, 611.

CHN-elementary analysis: C, 52.44; H, 5.03; N, 15.21.
Fe-content: 10.12% [m/m]
chloride-content: 0.0% [m/m] (not detectable)

Example 9

Tris-(6-methylpyrazine-2-ol-1-oxide)iron(III)-complex

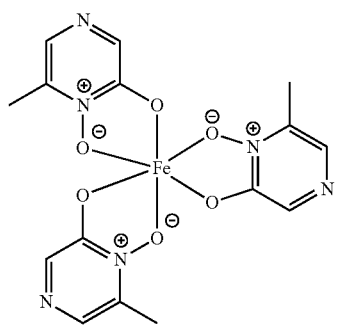

15.4 mmol (1.94 g) 6-methylpyrazine-2-ol-1-oxide were heated to reflux in 30 ml ethanol and 5.1 mmol (1.39 g) FeCl$_3$*6H$_2$O dissolved in 5 ml ethanol were added. Under reflux further 45 ml ethanol and 75 ml water were added dropwise, 120 ml solvent were distilled off and the reaction mixture was left for cooling. Subsequently pH 4.4 was adjusted with 15 ml 1 M NaOH, stirred for 30 min at 50° C., then the product was filtered off and dried. 2.1 g (92% Fe-yield) of the title compound were obtained.

IR (in substance, cm$^{-1}$): 1597, 1528, 1478, 1409, 1379, 1357, 1218, 1189, 1170, 1134, 1080, 1035, 989, 924, 861, 828, 712.

CHN-elementary analysis: C, 40.68; H, 3.48; N, 18.77.
Fe-content: 12.62% [m/m]
chloride-content: 0.0% [m/m] (not detectable)

Example 10

Tris-(3,6-dimethylpyrazine-2-ol-1-oxide)-iron(III)-complex

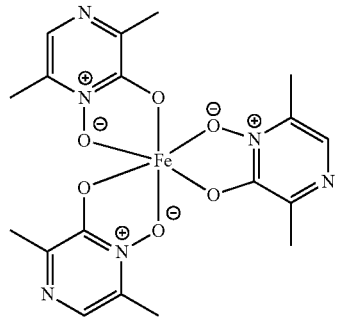

15 mmol (2.1 g) 3,6-dimethylpyrazine-2-ol-1-oxide were heated to reflux in 50 ml ethanol and 5 mmol (1.35 g) FeCl$_3$*6H$_2$O dissolved in 10 ml ethanol were added. Under reflux 50 ml water were added dropwise, 90 ml solvent were distilled off and the reaction mixture was left for cooling. Subsequently pH 4.4 was adjusted with 12 ml 1 M NaOH, the product was filtered off and dried. 2.2 g (87% Fe-yield) of the title compound were obtained.

IR (in substance, cm$^{-1}$): 1599, 1529, 1486, 1455, 1413, 1370, 1316, 1252, 1171, 1123, 1028, 978, 940, 859, 752, 707.

CHN-elementary analysis: C, 45.28; H, 4.31; N, 17.33.
Fe-content: 11.04% [m/m]
chloride-content: 0.0% [m/m] (not detectable)

Pharmacological Testing Method:

The excellent Fe utilizations that can be accomplished through the Fe complexes according to the invention were measured by means of the following mouse model.

Male NMRI (SPF) mice (approximately 3 weeks old) were fed a low-iron diet (approx. 5 ppm iron) for approximately 3 weeks. The iron complexes were then administered to them by means of a stomach tube (2 mg iron/kg body weight/day) for 2 times 5 days, with an interruption of 2 days (days 1-5 and 8-12). 6 mice were the control group (negative control) and were administered with water instead. Utilization on day 15 was calculated from the hemoglobin increase and the body weight increase in accordance with the formula $$\text{Utilization (\%)} = \frac{\Delta \text{iron utilization} * 100}{\text{Fe Dos.}} = \frac{(\text{Fe } ut. - \text{Fe } ut. \text{ Control}) * 100}{\text{Fe Dos.}} =$$

-continued $$[(Hb_{2(3)} \cdot BW_{9(14)} - Hb_1 \cdot BW_4) \cdot 0.07 \cdot 0.0034 -$$

$$(Hb_{2(3)Control} \cdot BW_{9(14)Control} - Hb_{1Control} \cdot BW_{4Control}) \cdot$$

$$0.07 \cdot 0.0034)] \cdot 100/Fe\ Dos. =$$

$$[(Hb_{2(3)} \cdot BW_{9(14)} - Hb_1 \cdot BW_4) \cdot 0.000238 -$$

$$(Hb_{2(3)Control} \cdot BW_{9(14)Control} - Hb_{1Control} \cdot BW_{4Control}) \cdot$$

$$0.000238] \cdot 100/Fe\ Dos. =$$

$$(Hb_{2(3)} \cdot BW_{9(14)} - Hb_1 \cdot BW_4 - Hb_{2(3)Control} \cdot BW_{9(14)Control} +$$

$$Hb_{1Control} \cdot BW_{4Control}) \cdot 0.0238/Fe\ Dos.$$

0.07 = Factor for 70 ml blood per kg body weight($BW$)

0.0034 = Factor for 0.0034 g Fe/g Hb $Hb_1$ = Hemoglobin level (g/l) on day 1

$Hb_{2(3)}$ = Hemoglobin level (g/l) on day 8 (or 15)

$BW_4$ = body weight (g) on day 1

$BW_{9(14)}$ = body weight (g) on day 8 (or 15)

$Hb_{1Control}$ = average hemoglobin level (g/l)

on day 1 in the control group, $Hb_{2(3)Control}$ = average hemoglobin level (g/l) on day 8

(or 15) in the control group, $BW_{4Control}$ = average body weight (g) on day 1 in the control group, $BW_{9(14)Contol}$ = average body weight (g) on day 8 (or 15) in the control group, Fe Dos. = entire adminstered iron (mg Fe) over 5 or 10 days, Fe ut. = $(Hb_{2(3)} \cdot BW_{9(14)} - Hb_1 \cdot BW_4) \cdot 0.07 \cdot 0.0034$ (mg Fe)

Δ Utilization= Fe tot. utilized (examined group) − Fe ut. Control group, utilized from food, (mg Fe)

The following table shows the results:

TABLE

| Example-No. | Utilization n 15 d (abs. %) | Standard deviation (+/−0.5) |
|---|---|---|
| 1 | 56 | 13 |
| 2 | 61 | 11 |
| 3 | 77 | 15 |
| 4 | 32 | 15 |
| 5 | 37 | 7 |
| 10 | 58 | 16 |
| Comparative Example* | 25 | 13 |

*COMPARATIVE EXAMPLE

As a comparative example the tris(pyridinone-2-ol-1-oxide)-iron (III)-complex compound of the formula:

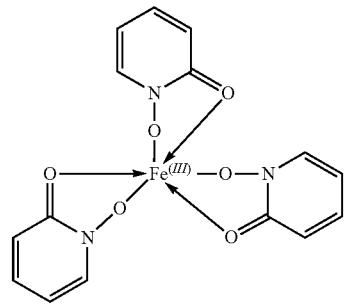

was prepared in analogy to EP 0138420 and tested, to show the influence of the heterocyclic basic structure. In Example 7 EP 0138420 discloses only tris(pyridinone-2-ol-1-oxide)-iron (III)-complex compounds which carry a further substituent at the pyridine ring. The unsubstituted tris(pyridinone-2-ol-1-oxide)iron(III)-complex compound, which is the present comparative example, is not disclosed therein.

As shown in the results in the table above, the corresponding pyrimidine compound of Example 1 of the present invention exhibits a significantly improved iron utilization compared to the pyridine comparative compound in analogy to EP 0138420. The Example compounds 2, 3, 4, 5 and 10 of the present invention show improved iron utilization compared to the comparative compound, too.

The measured iron utilization values are an important parameter with respect to the indication of the treatment of iron deficiency symptoms and iron deficiency anemia, because this parameter does not only reflect the iron adsorption but also the relation between body weight and iron adsorption, which is particularly important when using adolescent animals in the animal model. If only the hemoglobin levels were examined, which are a measure for the effectively adsorbed iron, the amount which is based on the growth of the animals would remain unconsidered. Accordingly, the iron utilization is a more concrete measure, although iron utilization and hemoglobin level mostly do not correlate with each other. An examination solely of the iron serum level, which can be measured, too, is to be less considered as therewith a prediction about the amount of iron can be given, which reaches the body, but not about the amount thereof which can be used by the body.

The invention is further explained bby the following embodiments:
1. Iron(III)-pyrazine-2-ol-1-oxide complex compounds or pharmaceutically acceptable salts thereof for the use as medicaments.
2. Iron(III) complex compounds according to embodiment 1, containing at least one ligand of the formula (I):

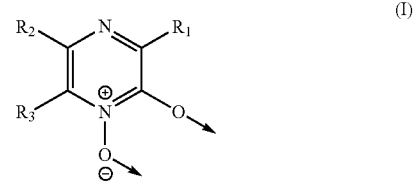

wherein
the arrows respectively represent a coordinate bond to one or different iron atoms, and R₁, R₂, R₃ may be the same or different and are selected from the group consisting of:
hydrogen,
halogen,
optionally substituted alkyl,
optionally substituted alkoxy,
optionally substituted aryl,
optionally substituted alkoxycarbonyl, and
optionally substituted aminocarbonyl or
R₂ and R₃ together with the carbon atoms to which they are bonded, form an optionally substituted saturated or unsaturated 5- or 6-membered ring, which may optionally contain one or more heteroatoms,
or pharmaceutically acceptable salts thereof.

3. Iron(III) complex compounds for use according to any one of embodiments 1 to 2, containing at least one ligand of the formula (I):

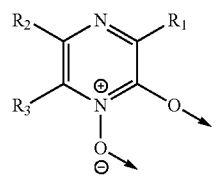

(I)

wherein
the arrows respectively represent a coordinate bond to one or different iron atoms, and
R₁, R₂, R₃ may be the same or different and are selected from the group consisting of:
hydrogen,
optionally substituted alkyl, and
halogen, or
R₂ and R₃ together with the carbon atoms to which they are bonded, form a 5- or 6-membered carbocyclic ring,
or pharmaceutically acceptable salts thereof.

4. Iron(III) complex compounds for use according to any one of embodiments 1 to 3, containing at least one ligand of the formula (I):

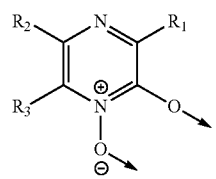

(I)

wherein
the arrows respectively represent a coordinate bond to one or different iron atoms, and
R₁, R₂, R₃ may be the same or different and are selected from the group consisting of hydrogen and alkyl, which may optionally be substituted by alkoxy, or
R₂ and R₃ together form a propylene (—CH₂—CH₂—CH₂—), butylene (—CH₂—CH₂—CH₂—CH₂—), azabutylene or oxabutylene group,
or pharmaceutically acceptable salts thereof.

5. Iron(III) complex compounds for use according to any one of embodiments 1 to 4, of the formula:

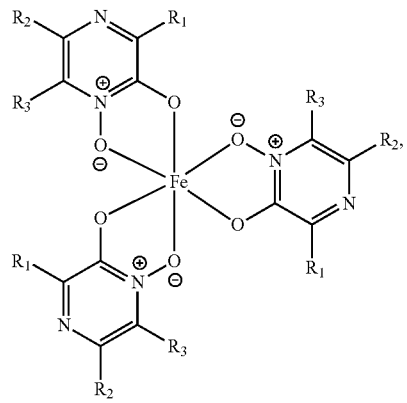

(II)

wherein R₁, R₂, R₃ may be the same or different and are defined as above, and pharmaceutically acceptable salts thereof.

6. Iron(III)-pyrazine-2-ol-1-oxide complex compounds, as defined in any of embodiments 1 to 5 in solid form.

7. Iron(III)-pyrazine-2-ol-1-oxide complex compounds according to embodiment 6 for use as a medicament.

8. Iron(III)-complex compounds for use according to any one of embodiments 1 to 5 and 7 for use in the treatment and prophylaxis of iron deficiency symptoms and iron deficiency anemias and the symptoms associated therewith.

9. Iron(III)-complex compounds for use according to embodiment 8, wherein the symptoms include: fatigue, listlessness, lack of concentration, low cognitive efficiency, difficulties in finding the right words, forgetfulness, unnatural pallor, irritability, acceleration of heart rate (tachycardia), sore or swollen tongue, enlarged spleen, desire for strange foods (pica), headaches, lack of appetite, increased susceptibility to infections, depressive moods.

10. Iron(III)-complex compounds for use according to embodiment 8 for the treatment of iron deficiency anemia in pregnant women, latent iron deficiency anemia in children and adolescents, iron deficiency anemia caused by gastrointestinal abnormalities, iron deficiency anemia due to blood loss, such as gastrointestinal hemorrhage (e.g. due to ulcers, carcinoma, hemorrhoids, inflammatory disorders, taking of acetylsalicylic acid), iron deficiency anemia caused by menstruation, iron deficiency anemia caused by injuries, iron deficiency anemia due to psilosis (sprue), iron deficiency anemia due to reduced dietary iron uptake, in particular in selectively eating children and adolescents, immunodeficiency caused by iron deficiency anemia, brain function impairment caused by iron deficiency anemias, restless leg syndrome caused by iron deficiency anemias, iron deficiency anemias in the case of cancer, iron deficiency anemias caused by chemotherapies, iron deficiency anemias triggered by inflammation (AI), iron deficiency anemias in the case of congestive cardiac insufficiency (CHF; congestive heart failure), iron deficiency anemias in the case of chronic renal insufficiency stage 3-5 (CKD 3-5; chronic kidney diseases stage 3-5), iron deficiency anemias triggered by chronic inflammation (ACD), iron deficiency anemias in the case of rheumatoid arthritis (RA; rheumatoid arthritis), iron deficiency anemias in the case of systemic lupus erythematosus (SLE; systemic lupus erythematosus) and iron deficiency anemias in the case of inflammatory bowel diseases (IBD; inflammatory bowel diseases).
11. Iron(III)-complex compounds for use according to any one of embodiments 1 to 5 and 7 to 10, wherein the iron(III) complex compound is administered orally.
12. Iron(III)-complex compounds for use according to embodiment 11, which is administered in the form of a tablet or a capsule, including enteric coated forms or forms with pH-dependent coatings.
13. Medicament, containing iron(III) complex compounds as defined in any one of embodiments 1 to 6.
14. Medicament, containing iron(III) complex compounds as defined in any one of embodiments 1 to 6 and at least one physiological compatible carrier or excipient.
15. Composition containing iron(III) complex compounds as defined in any one of embodiments 1 to 6, in combination with at least one further medicament which acts on the iron metabolism.

The invention claimed is:
1. A method for treatment of iron deficiency and iron deficiency anemia by supplying iron to a patient in need thereof, the method comprising the step of:
administering iron (III)-pyrazine-2-ol-1-oxide complex compounds or pharmaceutically acceptable salts thereof, which contain at least one ligand of the formula (I):

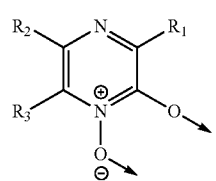

wherein
the arrows respectively represent a coordinate bond to one or different iron atoms, and $R_1$, $R_2$, $R_3$ may be the same or different and are selected from the group consisting of:
hydrogen,
halogen,
alkyl, which may be substituted with 1 to 3 substituents selected from hydroxy, aryl, heteroaryl, alkoxy, alkoxycarbonyl, acyl, halogen, amino, aminocarbonyl and cyano,
alkoxy, which may be substituted with 1 to 3 substituents selected from hydroxy, aryl, heteroaryl, alkoxy, alkoxycarbonyl, acyl, halogen, amino, aminocarbonyl and cyano,
aryl, which may be substituted with 1 or 2 substituents, selected from halogen, hydroxy, alkyl, and alkoxy,
alkoxycarbonyl, which may be substituted with 1 to 3 substituents selected from hydroxy, aryl, heteroaryl, alkoxy, alkoxycarbonyl, acyl, halogen, amino, aminocarbonyl and cyano, and
aminocarbonyl, which may be substituted with 1 to 3 substituents selected from hydroxy, aryl, heteroaryl, alkoxy, alkoxycarbonyl, acyl, halogen, amino, aminocarbonyl and cyano, or
$R_2$ and $R_3$ together with the carbon atoms to which they are bonded, form a saturated or unsaturated 5- or 6-membered ring, which may be substituted by 1 to 3 substituents selected from hydroxy, oxo, $C_1$-$C_4$-alkoxy, amino, mono- or di-($C_1$-$C_4$-alkyl)amino, and which may optionally contain one or more heteroatoms, or pharmaceutically acceptable salts thereof.

2. The method of claim 1, wherein the arrows respectively represent a coordinate bond to one or different iron atoms, and
$R_1$, $R_2$, $R_3$ may be the same or different and are selected from the group consisting of:
hydrogen,
the alkyl of claim 1, and
halogen, or
$R_2$ and $R_3$ together with the carbon atoms to which they are bonded, form a 5- or 6-membered carbocyclic ring, or pharmaceutically acceptable salts thereof.

3. The method of claim 1, wherein the arrows respectively represent a coordinate bond to one or different iron atoms, and
$R_1$, $R_2$, $R_3$ may be the same or different and are selected from the group consisting of hydrogen and alkyl, which may optionally be substituted by alkoxy, or
$R_2$ and $R_3$ together form a propylene (—$CH_2$—$CH_2$—$CH_2$—), butylene (—$CH_2$—$CH_2$—$CH_2$—$CH_2$—), azabutylene or oxabutylene group, or pharmaceutically acceptable salts thereof.

4. The method of claim 1, wherein the iron (III) complex compound has the formula:

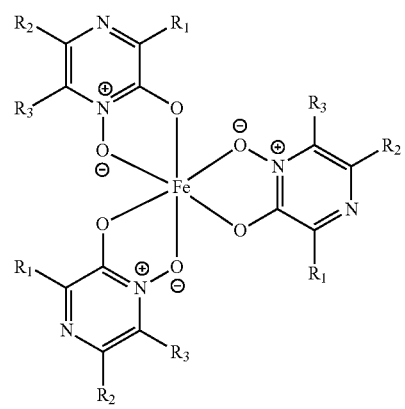

5. The method of claim 1, wherein the iron (III)-pyrazine-2-ol-1-oxide complex compounds are administered in solid form.

6. The method of claim 1, wherein the iron(111)-complex compounds or pharmaceutically acceptable salts thereof are administered for the treatment of fatigue, listlessness, lack of concentration, low cognitive efficiency, difficulties in finding the right words, forgetfulness, unnatural pallor, irritability, acceleration of heart rate (tachycardia), sore or swollen tongue, enlarged spleen, desire for strange foods (pica), headaches, lack of appetite, increased susceptibility to infections, and depressive moods.

7. The method of claim 1, wherein the treatment is selected from the group consisting of: treatment of iron deficiency anemia in pregnant women, latent iron deficiency anemia in children and adolescents, iron deficiency anemia caused by gastrointestinal abnormalities, iron deficiency anemia due to blood loss, iron deficiency anemia due to gastrointestinal hemorrhage iron deficiency anemia due to ulcers, carcinoma, hemorrhoids, inflammatory disorders, or taking of acetylsalicylic acid, iron deficiency anemia caused by menstruation, iron deficiency anemia caused by injuries, iron deficiency anemia due to psilosis (sprue), iron deficiency anemia due to reduced dietary iron uptake, iron deficiency anemia due to reduced dietary iron uptake in selectively eating children and adolescents, immunodeficiency caused by iron deficiency anemia, brain function impairment caused by iron deficiency anemias, restless leg syndrome caused by iron deficiency anemias, iron deficiency anemias in the case of cancer, iron deficiency anemias caused by chemotherapies, iron deficiency anemias triggered by inflammation (AI), iron deficiency anemias in the case of congestive cardiac insufficiency (CHF; congestive heart failure), iron deficiency anemias in the case of chronic renal insufficiency stage 3-5 (CKD 3-5; chronic kidney diseases stage 3-5), iron deficiency anemias triggered by chronic inflammation (ACD), iron deficiency anemias in the case of rheumatoid arthritis (RA; rheumatoid arthritis), iron deficiency anemias in the case of systemic lupus erythematosus (SLE; systemic lupus erythematosus) and iron deficiency anemias in the case of inflammatory bowel diseases (IBD; inflammatory bowel diseases).

8. The method of claim 1, wherein the administration is carried out orally.

9. The method of claim 8, wherein the administration is carried out in the form of a tablet or a capsule, including enteric coated forms or forms with pH-dependent coatings.

10. The method of claim 1, wherein the administration is carried out in the form of a pharmaceutical preparation containing at least one physiological compatible carrier or excipient.

* * * * *